US010046324B2

(12) United States Patent
Rankin et al.

(10) Patent No.: US 10,046,324 B2
(45) Date of Patent: Aug. 14, 2018

(54) REAGENT MAGAZINE WITH MOTOR LATCH COUPLER

(71) Applicant: Colder Products Company, Saint Paul, MN (US)

(72) Inventors: William J. Rankin, Burnsville, MN (US); Robert Keith Johnson, Blaine, MN (US)

(73) Assignee: Colder Products Company, St. Paul, MN (US)

( * ) Notice: Subject to any disclaimer, the term of this patent is extended or adjusted under 35 U.S.C. 154(b) by 603 days.

(21) Appl. No.: 14/512,709

(22) Filed: Oct. 13, 2014

(65) Prior Publication Data

US 2015/0135502 A1 May 21, 2015

Related U.S. Application Data

(60) Provisional application No. 61/890,501, filed on Oct. 14, 2013.

(51) Int. Cl.
| | |
|---|---|
| *B01L 3/00* | (2006.01) |
| *B41J 2/175* | (2006.01) |
| *G03G 21/16* | (2006.01) |
| *G01N 35/10* | (2006.01) |
| *F16L 37/098* | (2006.01) |
| *G03G 15/08* | (2006.01) |
| *B41J 29/38* | (2006.01) |

(52) U.S. Cl.
CPC .............. *B01L 3/527* (2013.01); *B41J 2/1752* (2013.01); *B41J 2/17523* (2013.01); *B41J 2/17553* (2013.01); *B41J 29/38* (2013.01); *F16L 37/0982* (2013.01); *G01N 35/1002* (2013.01); *G03G 15/0865* (2013.01); *G03G 21/1647* (2013.01); *G03G 21/1676* (2013.01); *B01L 2200/025* (2013.01); *B01L 2200/04* (2013.01); *B01L 2200/16* (2013.01); *B01L 2300/0609* (2013.01); *B41J 2/175* (2013.01); *B41J 2/1754* (2013.01); *B41J 2/17593* (2013.01); *Y10T 29/49817* (2015.01)

(58) Field of Classification Search
CPC ....................................................... B41J 2/1752
See application file for complete search history.

(56) References Cited

U.S. PATENT DOCUMENTS

| | | |
|---|---|---|
| 5,033,777 A | 7/1991 | Blenkush |
| 6,649,829 B2 | 11/2003 | Garber et al. |

(Continued)

FOREIGN PATENT DOCUMENTS

WO 2012/012779 A2 1/2012

OTHER PUBLICATIONS

International Search Report and Written Opinion for Application No. PCT/US2014/060278 dated Jan. 19, 2015.

*Primary Examiner* — P. Kathryn Wright
(74) *Attorney, Agent, or Firm* — Fish & Richardson P.C.

(57) ABSTRACT

A motorized latch assembly includes an electric motor, an eccentric cam attached via gears to a shaft of the motor and a latch plate configured to lock the reagent cartridge to the coupler. The eccentric cam is rotated when the shaft of the motor rotates. When the eccentric cam is rotated so that the eccentric cam presses down upon the latch plate, the latch plate moves a sufficient distance to permit the reagent cartridge to be disconnected from the coupler.

16 Claims, 30 Drawing Sheets

(56) References Cited

U.S. PATENT DOCUMENTS

| | | | |
|---|---|---|---|
| 2007/0263246 A1* | 11/2007 | Bressan | G06F 3/1219 358/1.15 |
| 2008/0003140 A1 | 1/2008 | Di et al. | |
| 2008/0239034 A1* | 10/2008 | Umeda | B41J 2/17509 347/86 |
| 2009/0039002 A1 | 2/2009 | Umeda | |
| 2010/0085404 A1* | 4/2010 | Akiyama | B41J 2/17513 347/86 |
| 2012/0168305 A1 | 7/2012 | Hunter | |

* cited by examiner

REAGENT MAGAZINE WITH MOTOR LATCH COUPLER

CROSS-REFERENCE TO RELATED APPLICATIONS

This application claims priority to U.S. Application Ser. No. 61/890,501, filed on Oct. 14, 2013. The disclosure of the prior application is considered part of the disclosure of this application, and is incorporated in its entirety into this application.

BACKGROUND

A reagent magazine is a physical assembly that may hold one or more cartridges containing reagent material. The reagent magazine may be used to dispense reagents from the cartridges to a receiving device coupled to the reagent magazine.

As a prerequisite to dispensing reagent, a flow path needs to be established between each cartridge and the receiving device. Typically a physical connection is made between each cartridge and a coupler located either in the reagent magazine or the receiving device. The physical connection typically requires opening a latch plate in a female coupler so that a male coupler on the cartridge can fit through the female coupler.

SUMMARY

According to one aspect, a motorized latch assembly comprises: an electric motor; an eccentric cam attached via gears to a shaft of the motor, the eccentric cam being rotated when the shaft of the motor rotates; a coupler for coupling a reagent cartridge to a receiving device; and a latch plate configured to lock the reagent cartridge to the coupler, wherein, when the eccentric cam is rotated so that the eccentric cam presses down upon the latch plate, the latch plate moves a sufficient distance to permit the reagent cartridge to be physically disconnected from the coupler.

According to another aspect, a method for disconnecting a reagent cartridge from a reagent receiving device comprises: physically connecting a coupler to the reagent receiving device, the coupler being part of a motorized latch assembly of a reagent magazine, the reagent magazine including a plurality of reagent cartridges; detecting that the reagent cartridge has been physically connected to the coupler; receiving a command to unlatch the coupler in the motorized latch assembly; after receiving the command, disconnecting the reagent cartridge from the coupler.

In yet another aspect, a system for automatically enabling a reagent cartridge to be physically connected to a reagent receiving device comprises: a reagent magazine; a motorized latch assembly, the motorized latch assembly comprising: an electric motor; an eccentric cam attached via gears to a shaft of the motor, the eccentric cam being rotated when the shaft of the motor rotates; a coupler for coupling a reagent cartridge to a receiving device; and a latch plate, the latch plate partially covering part of the first opening, the latch plate being configured to move away from the first opening when pressed down upon by the eccentric cam; a reagent receiving device; and a control device, wherein, when the eccentric cam is rotated so that the electric cam presses down upon the latch plate, the latch plate moves a sufficient distance to permit the reagent cartridge to be physically connected to the coupler.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Figure 1:
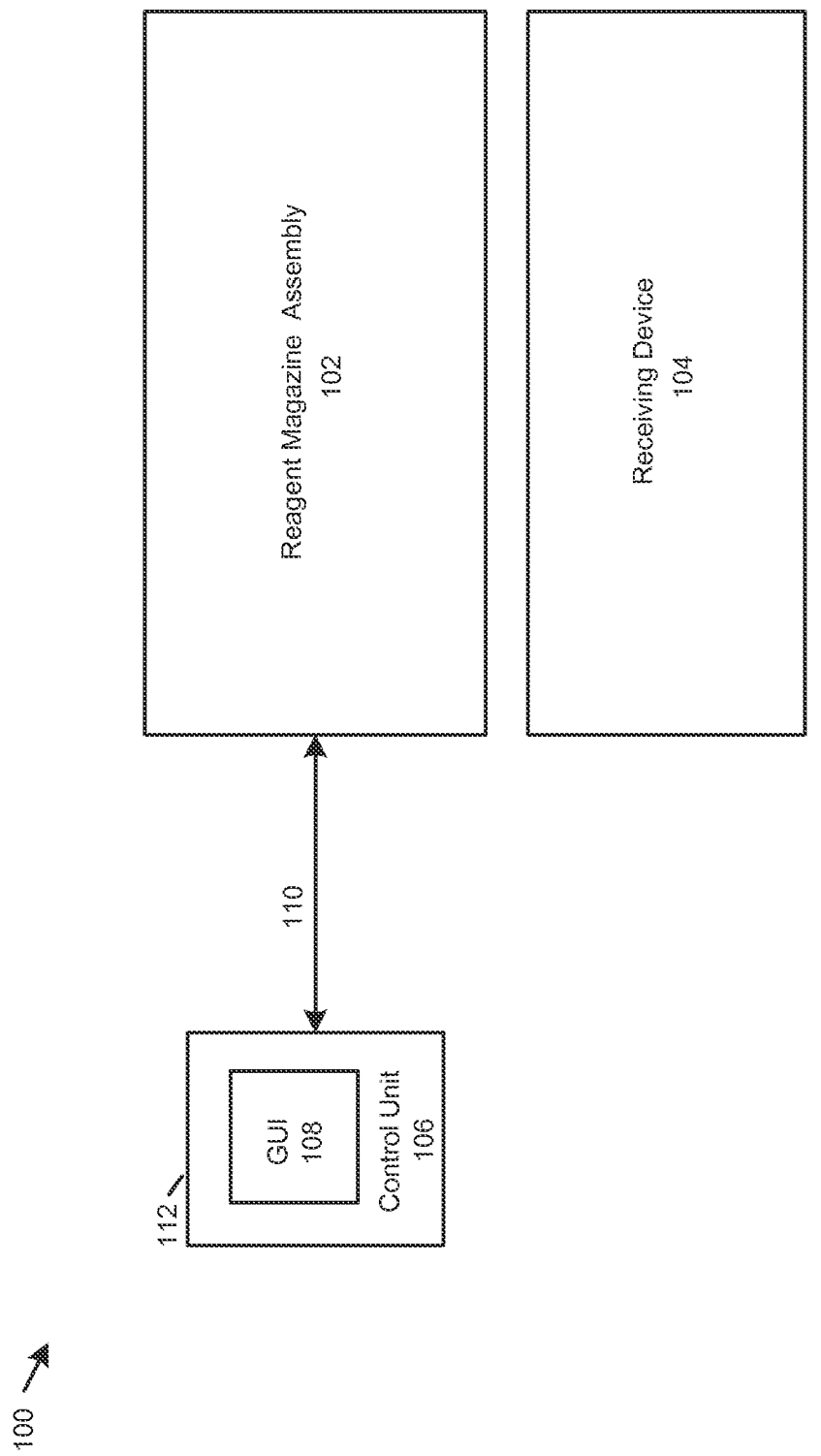
FIG. 1 is a block diagram of an example system that includes a reagent magazine and a motorized latch coupler.
Figure 2:
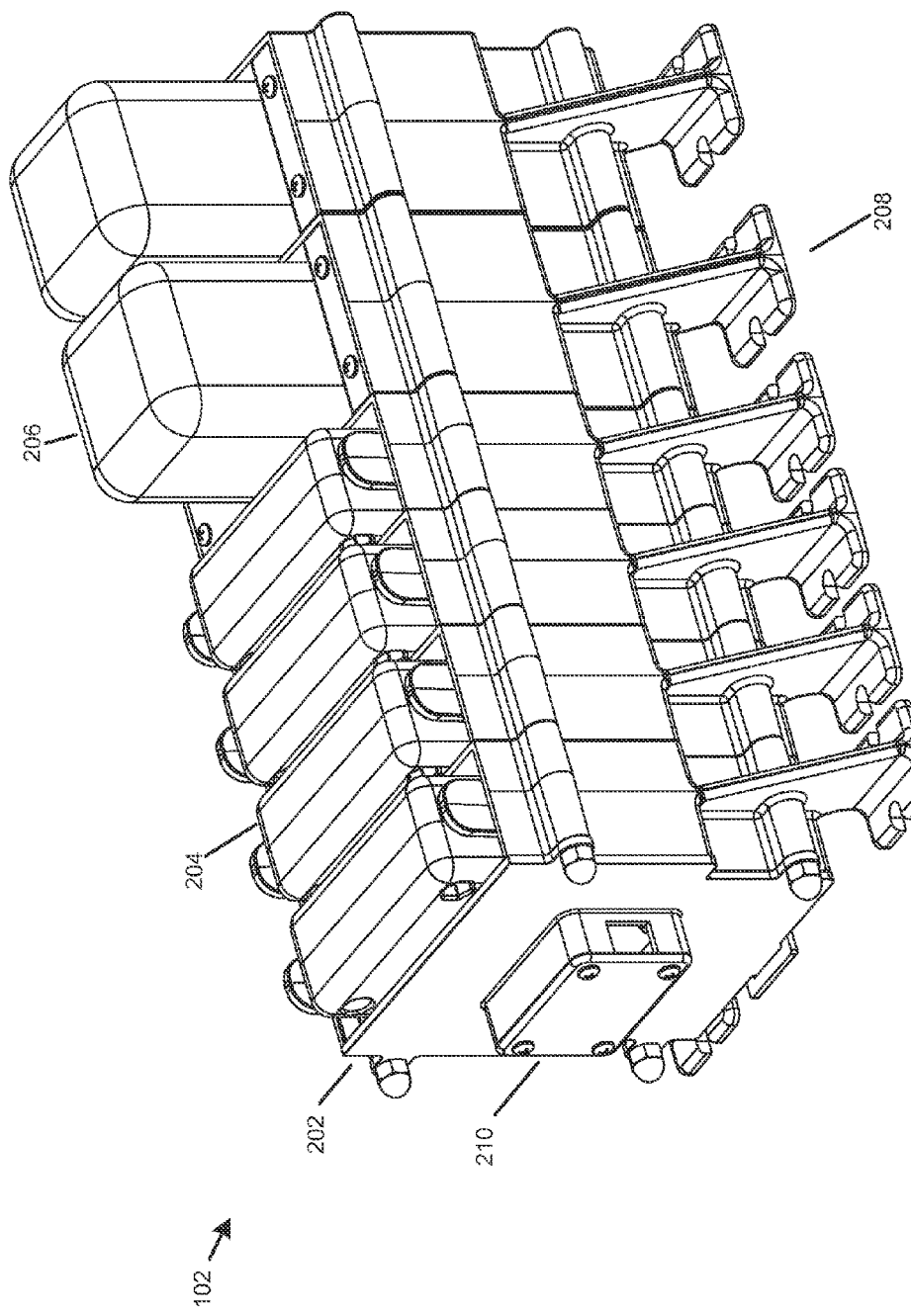
FIG. 2 is a perspective view of a reagent magazine assembly.
Figure 3:
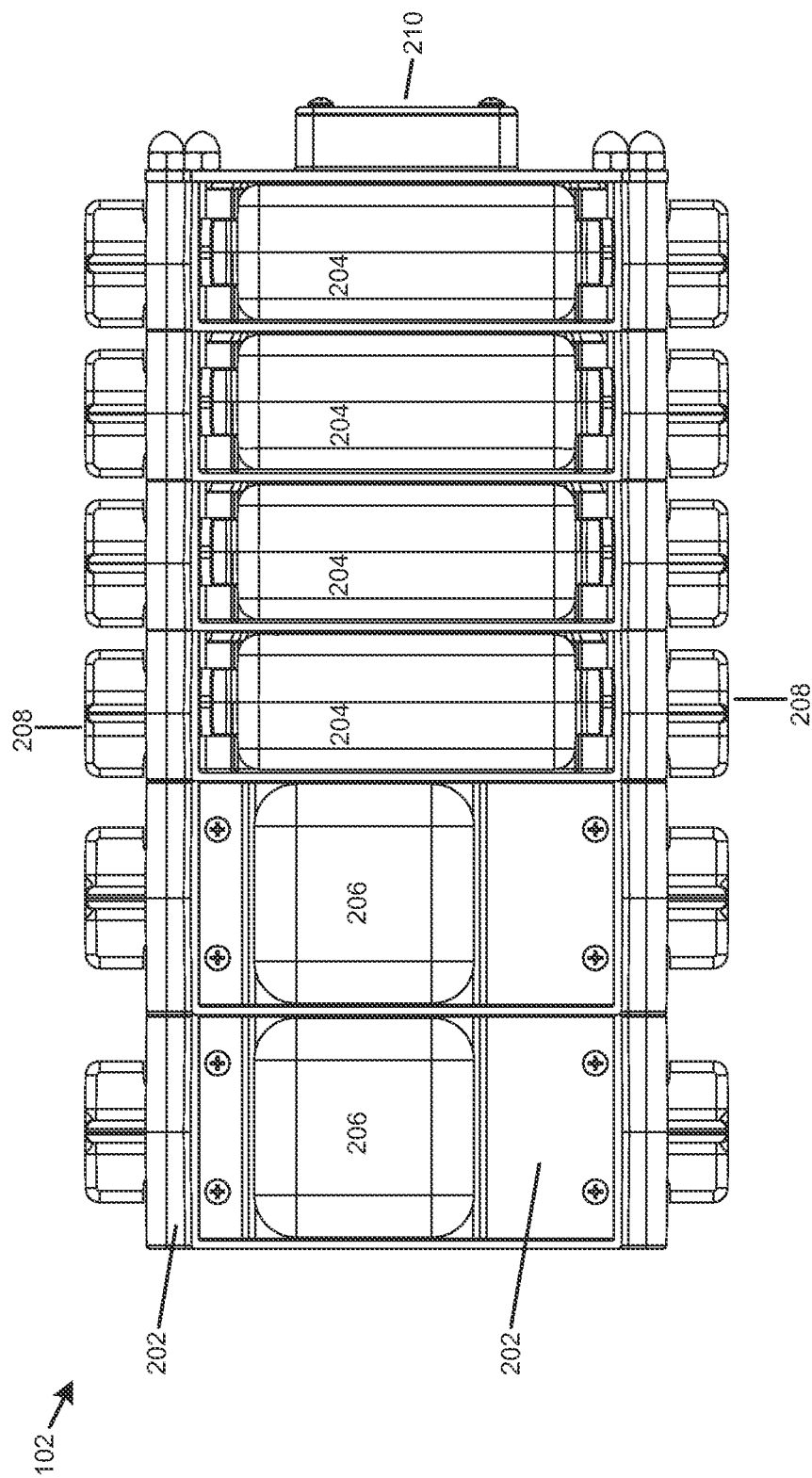
FIG. 3 is a top view of the reagent magazine assembly of FIG. 2.
Figure 4:
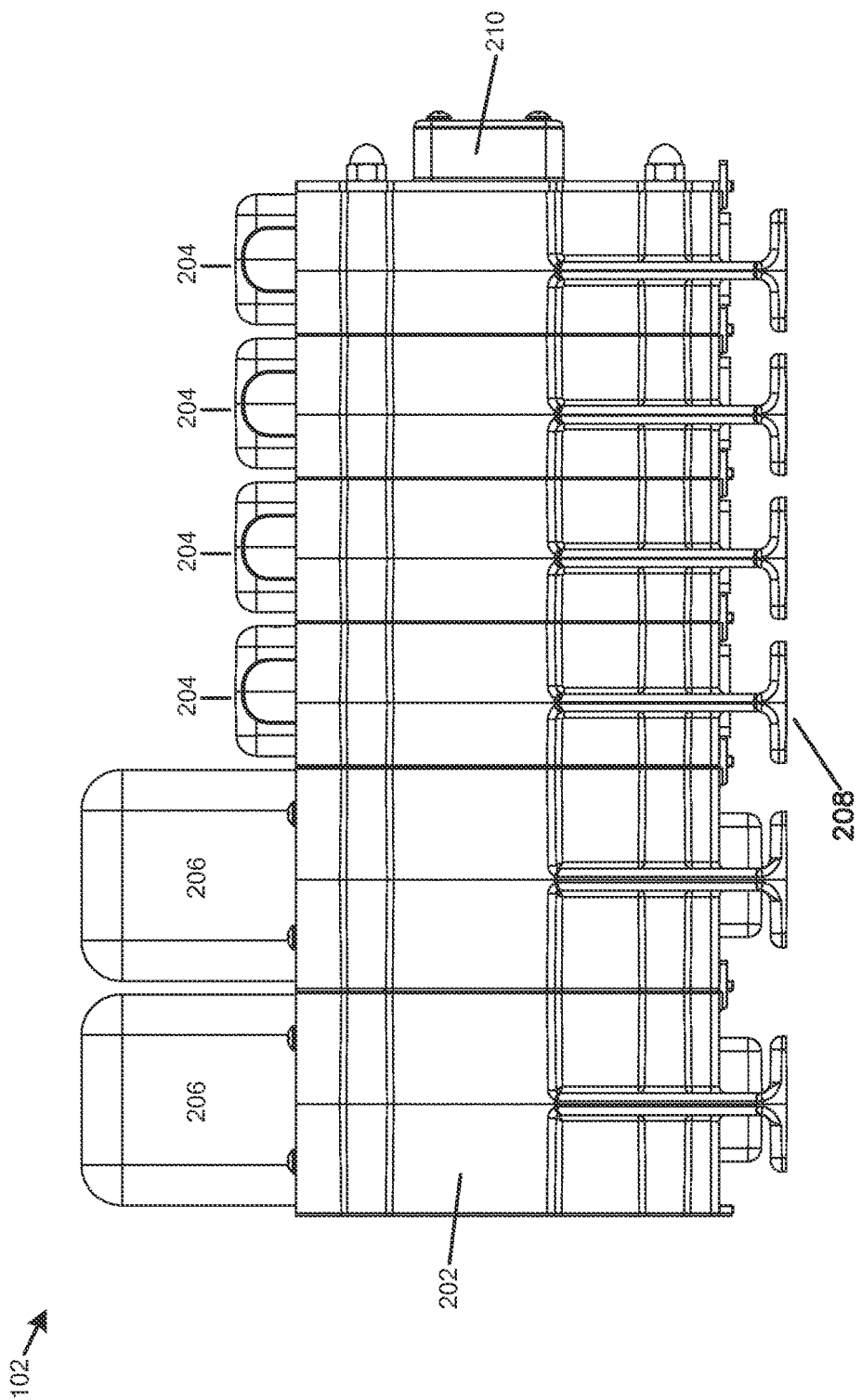
FIG. 4 is a rear view of the reagent magazine assembly of FIG. 2.
Figure 5:
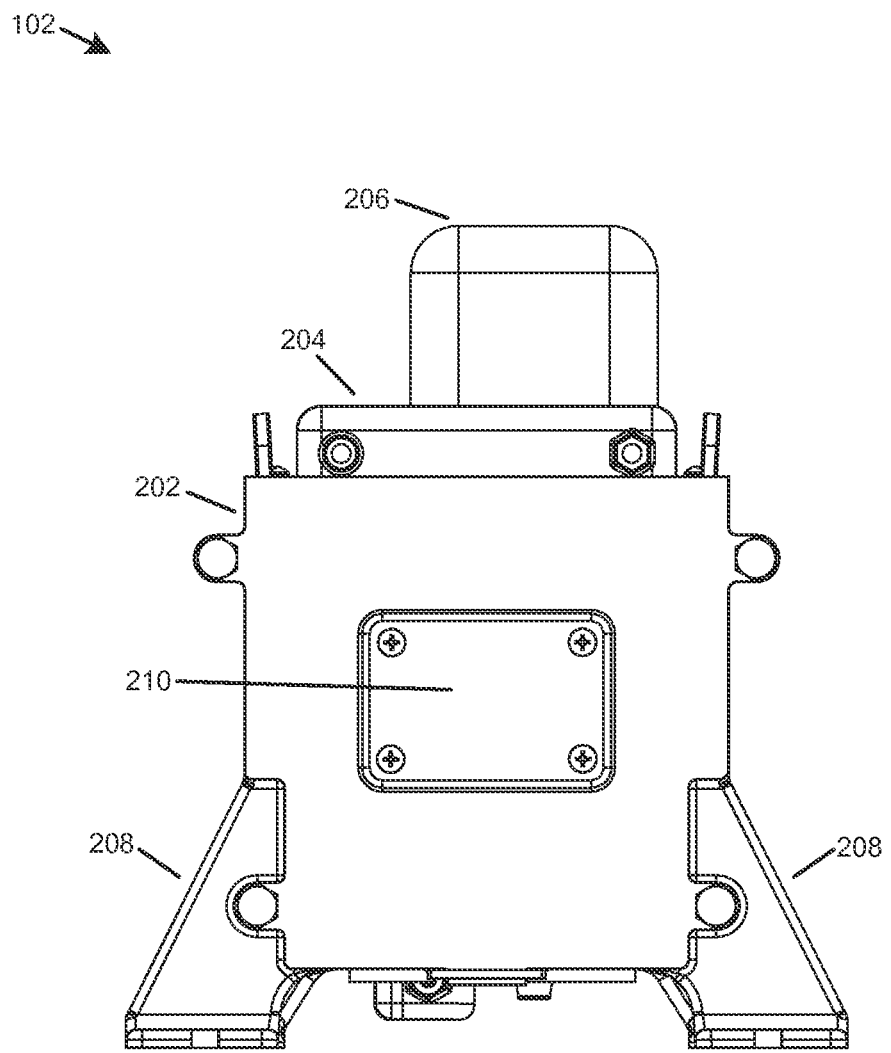
FIG. 5 is an end view of the reagent magazine assembly of FIG. 2.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The system and methods of the present disclosure are directed to a motorized latch for a reagent magazine. The motorized latch permits a cartridge in the reagent magazine to be coupled to a receiving device that receives and uses a reagent. Examples of receiving devices are printers, laboratory devices or other similar devices that use reagent. Receiving devices may also be used to receive waste (e.g. completed tests, solvents and cleaners).

The motorized latch is normally spring-biased to a closed position. When the motorized latch is in the closed position, the cartridge may be physically inserted into a coupler in a motorized latch assembly. The force of inserting the cartridge into the coupler is sufficient to temporarily move the motorized latch to an open position, permitting a portion of the cartridge to be inserted into the coupler. When the cartridge is inserted into the coupler while in the closed position, the cartridge is locked in the coupler and prevented from being removed from the coupler. When the motorized latch is set to an open position, the cartridge may be removed from the coupler. The motorized latch is electronically controlled, typically thorough a graphical user interface (GUI) on an electronic computing device. Because the motorized latch is electronically controlled, the cartridge may be remotely enabled to be connected to the receiving device or removed from the receiving device.

Referring now to FIG. 1, an example system 100 is shown. System 100 includes a reagent magazine assembly 102, a receiving device 104, a control unit 106 and a graphical user interface (GUI) 108. The reagent magazine assembly 102 provides a receptacle for one or more cartridges that contain reagent. A reagent is any type of fluid that can be delivered from the reagent magazine assembly 102 to the receiving device 104, as described herein.

A plurality of different sized cartridges may be used. Receiving device 104 receives reagent from the cartridges. The control unit 106 and GUI 108 are part of an electronic computing device 112, for example a desktop or laptop computer or a mobile device.

The control unit 106 controls the exit of the cartridges from the receiving device 104. In some embodiments, the control unit 106 may also control the entry of the cartridges to receiving device 104. The control unit is operated through the GUI 108. Upon activation at the GUI 108, a physical connection is enabled between a coupler in a cartridge and a coupler in the reagent magazine assembly 102. The physical connection is actually made when the cartridge is manually inserted into the coupler. The physical connection establishes a pathway for reagent to flow from the cartridge to receiving device 104. A physical connection may be made between each of the cartridges and receiving device 104. In this disclosure, the content of each cartridge is referred to as reagent. However, other types of content may be included in the cartridges instead of reagent.

For example, in one embodiment, the receiving device 104 is a printer that receives reagent (e.g., toner or ink) from a cartridge. In another embodiment, the receiving device is a laboratory device that receives reagent (e.g., a chemical compound) from a cartridge. The reagent magazine assembly 102 is mounted to the receiving device 104, so that, for example, reagent from a cartridge flows into a printer or a laboratory device.

FIG. 1 also shows an electrical connection 110 between the control unit 106 and the reagent magazine assembly 102. The electrical connection 110 is typically a hard-wired connection. The electrical connection permits the reagent magazine assembly 102 to be controlled from the GUI 108 of control unit 106, as explained in detail later herein.

However, in some embodiments, a wireless connection, such as a Bluetooth connection, may be used. The wireless connection may permit the reagent magazine assembly 102 to be controlled from a mobile device such as a smart telephone or a tablet computer. In some embodiments, the smart telephone may support voice control, permitting the reagent magazine assembly 102 to be voice controlled by the smart telephone.

Referring now to FIGS. 2-5, the example reagent magazine assembly 102 is shown. The reagent magazine assembly 102 includes a chassis 202, four cartridges 204 of a first size, two cartridges 206 of a second size, brackets 208 for securing the reagent magazine assembly 102 to the receiving device 104 and an electrical assembly 210 for connecting the reagent magazine to the control unit 106. Each of the cartridges 204, 206 fits into a slot in the reagent magazine assembly 102. More or fewer cartridges may be used. Smaller, larger and different sized and shaped cartridges may be used. In this disclosure, cartridges 204 and 206 may be referred to both in a singular tense (for example when referring to a cartridge 204) or in a plural sense (for example when referring to a plurality of cartridges—cartridges 204).

Figure 6:
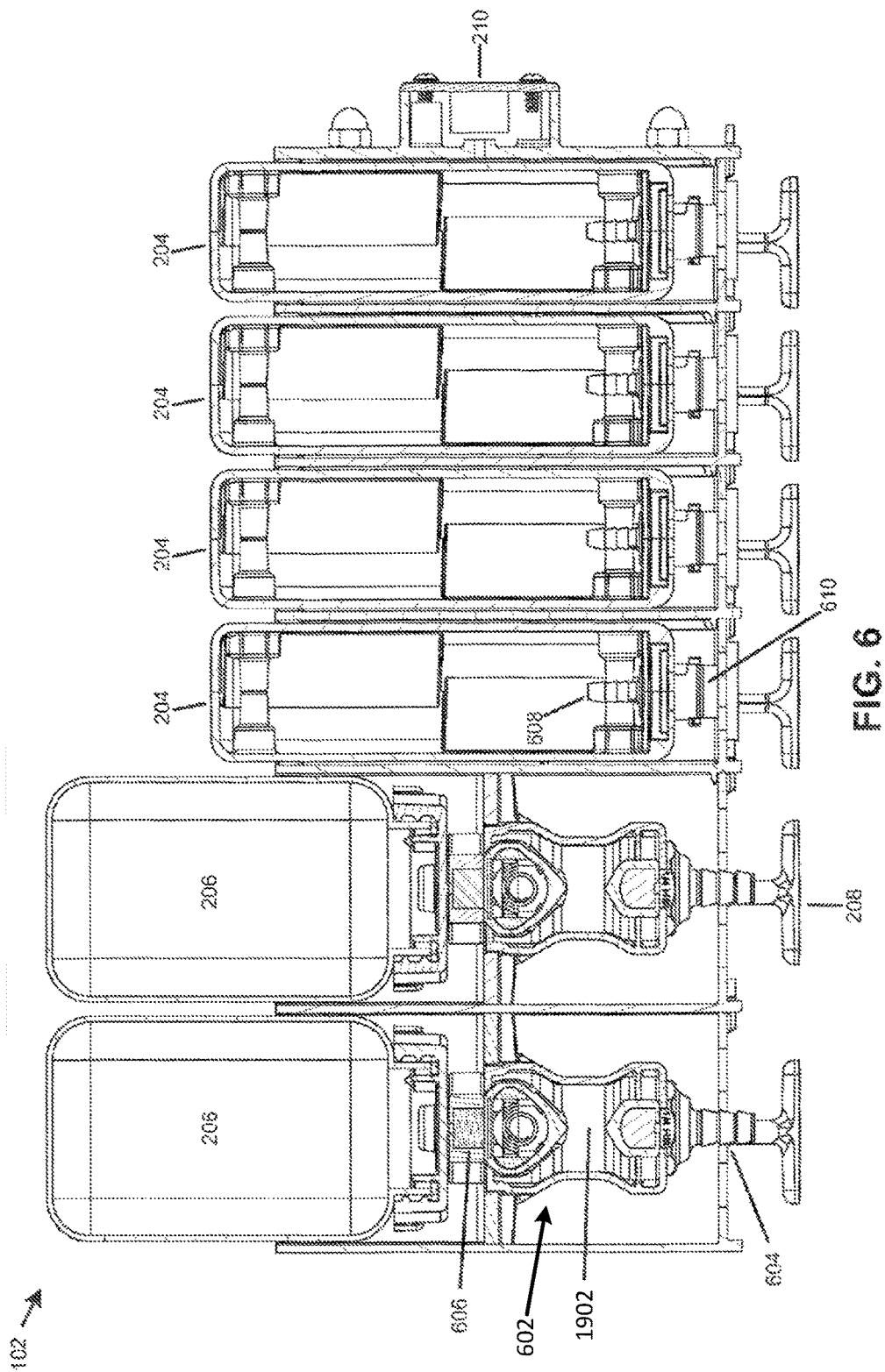
FIG. 6 is a cross-section drawing of the reagent magazine assembly of FIG. 2.
Figure 7:
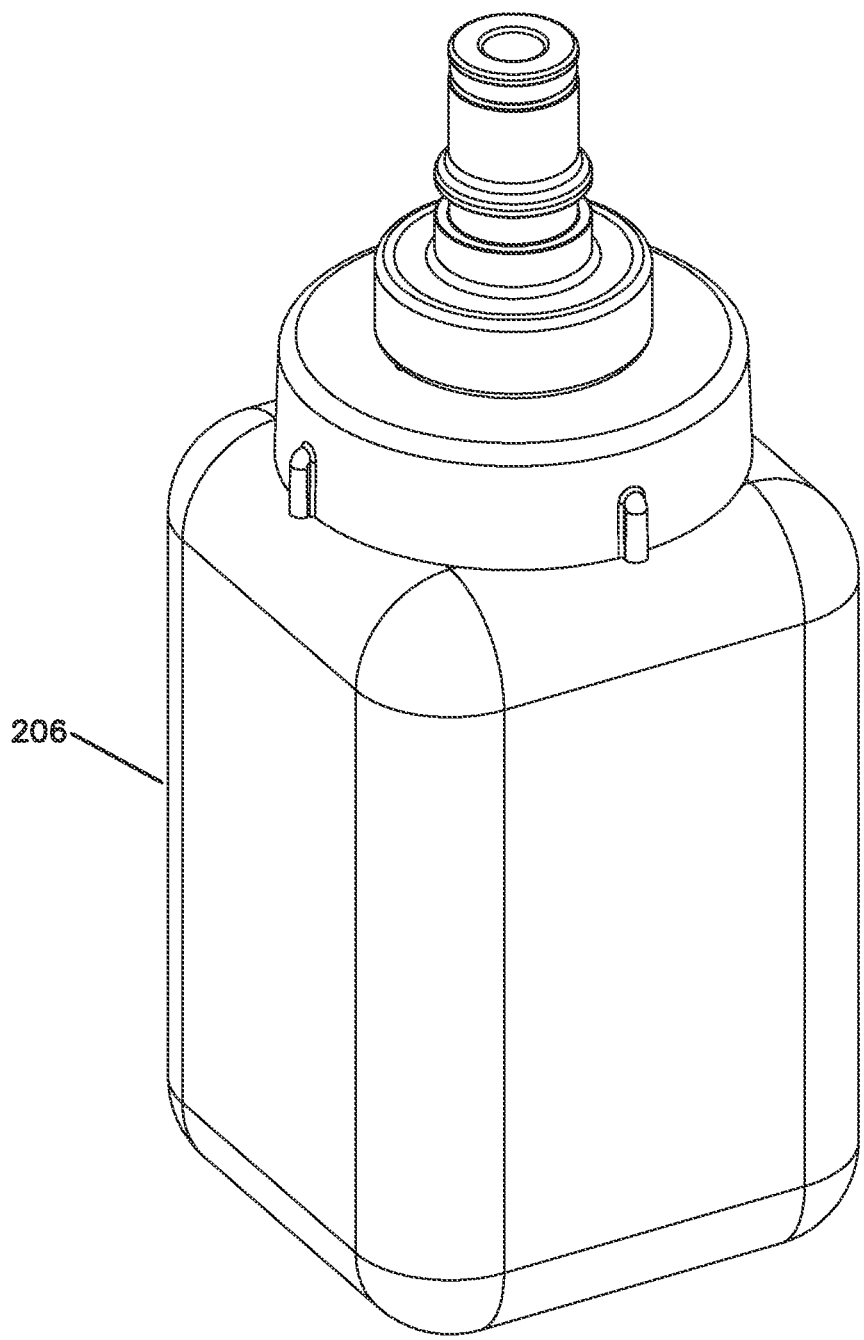
FIG. 7 is a perspective view of a large cartridge assembly of the reagent magazine assembly of FIG. 2.
Figure 8:
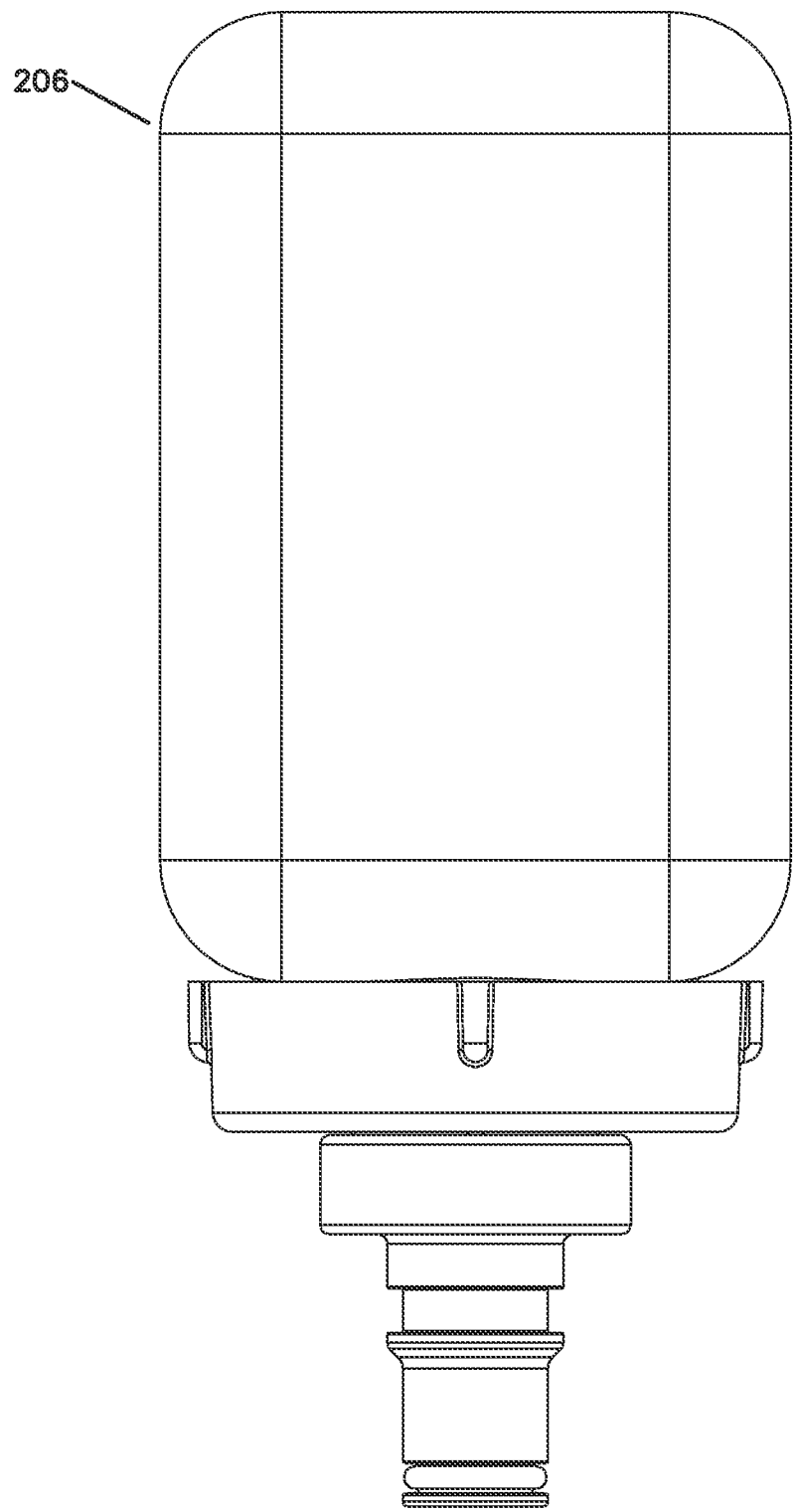
FIG. 8 is a side view of the cartridge assembly of FIG. 7.
Figure 9:
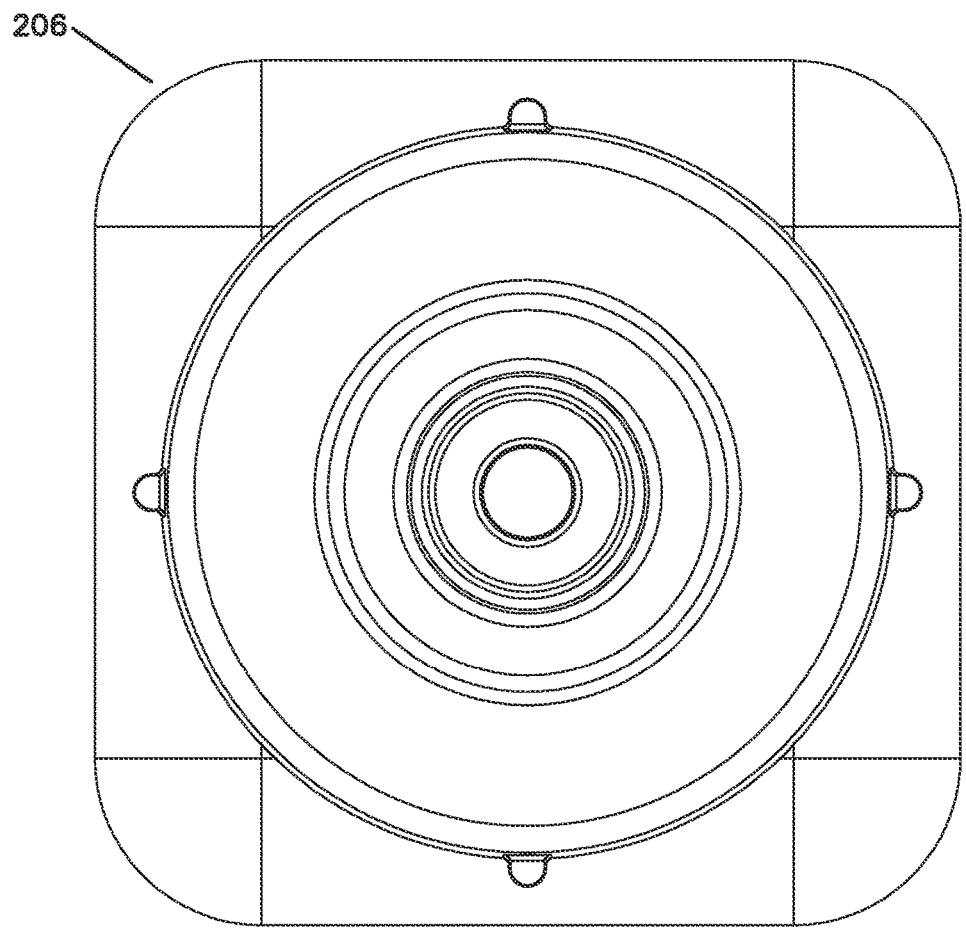
FIG. 9 is a top view of the cartridge assembly of FIG. 7.

Referring now to FIG. 6, the reagent magazine assembly 102 is shown in cross-section. An example motorized latch assembly 602 is depicted. The motorized latch assembly 602 is a coupler that physically connects a cartridge 206 to the receiving device 104. A termination 604 of each motorized latch assembly 602 is coupled to a conduit or other element (not shown) that moves the reagent from the cartridges 204, 206 to a desired location within the receiving device 104. As discussed in more detail later herein, the motorized latch assembly 602 includes a latch plate that can be automatically activated by control unit 106. As stated earlier herein, the latch plate is spring-biased to a closed position. Cartridge 206 may be inserted into a coupler 1902 in motorized latch assembly 602 and locked in the coupler 1902 when the latch plate is in the closed position. Typically, the latch plate is activated to remove a cartridge that is locked into the coupler 1902. When activated, a motor in the motorized latch assembly 602 moves the latch plate to an open position (i.e., down), permitting cartridge 206 to be removed from the coupler 1902 of the motorized latch assembly 602.

When a physical connection is made and cartridge 206 is inserted into the coupler 1902 of motorized latch assembly 602, an insert valve 606 of cartridge 206 engages a valve in the motorized latch assembly 602 to permit reagent to flow from cartridge 206, through motorized latch assembly 602 to receiving device 104. As shown in FIG. 6, motorized latch assemblies are not used for cartridge 204, although they may be used for cartridge 204 in other embodiments. Instead, reagent flows through an insert tube 608 in cartridge 204, through insert 610, to the receiving device 104. Insert 610 is typically physically attached directly to a corresponding structure (e.g., coupler—not shown) on the receiving device 104. Other configurations are possible.

Cartridge 206 may also be inserted into the coupler 1902 of the motorized latch assembly 602 when the latch plate is in the open position. However, when cartridge 206 is inserted into the coupler 1902 when the latch plate is in the open position, cartridge 206 needs to be held in the coupler 1902 until the latch plate is closed.

Figure 10:
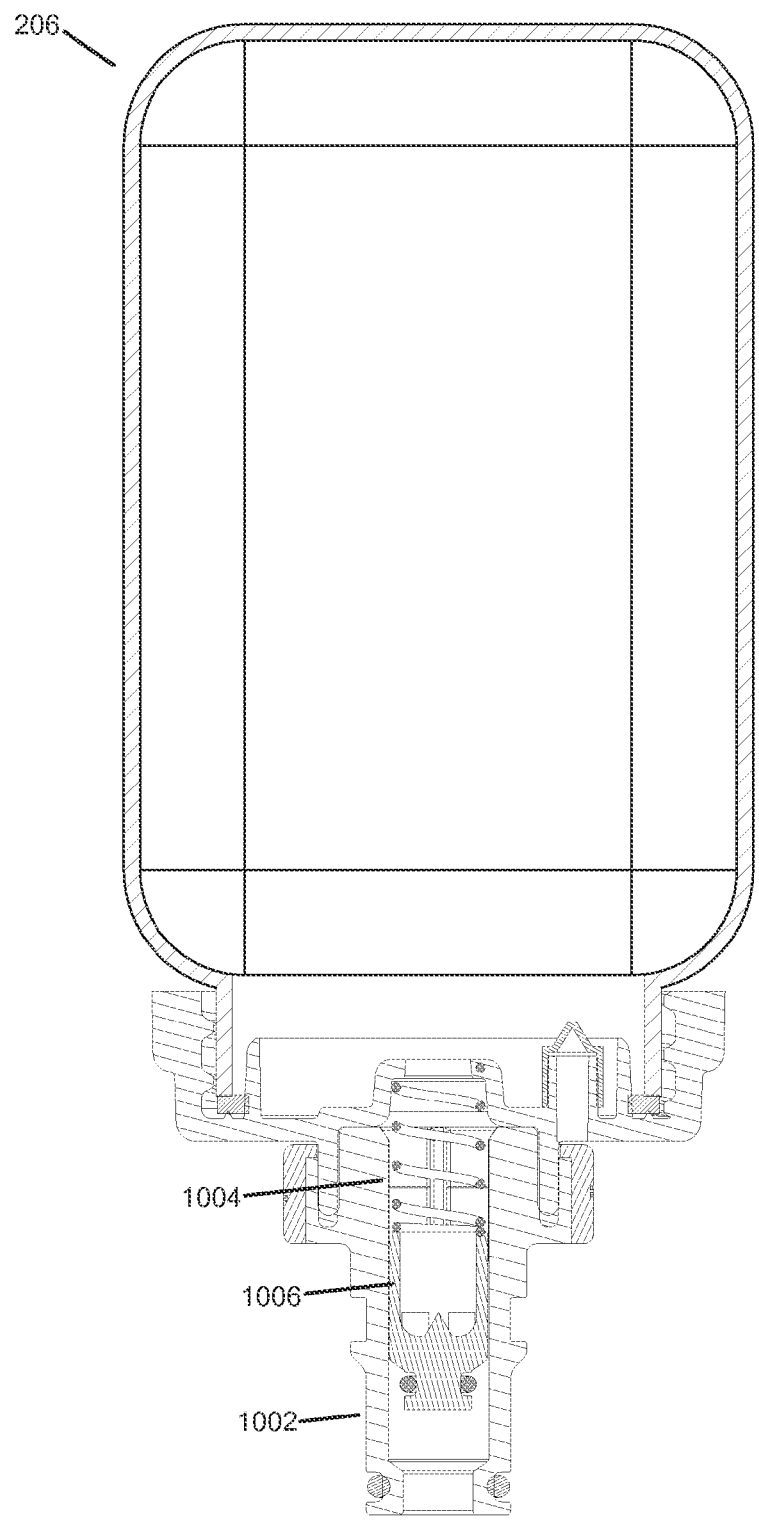
FIG. 10 is a cross-section drawing of the cartridge assembly of FIG. 7.

FIGS. 7-10 show the cartridge 206. Referring now to FIG. 10, a cross-section drawing is shown for cartridge 206. Cartridge 206 includes an insert 1002, a spring 1004 and a valve cylinder 1006. The insert 1002 is physically connected to the coupler of the motorized latch assembly 602 and inserted into the coupler of the motorized latch assembly 602 when the latch plate is activated by control unit 106, as discussed in detail later herein in conjunction with FIGS. 19-25. When insert 1002 is inserted into the coupler of the motorized latch assembly 602, spring 1004 is compressed. The compression of spring 1004 moves valve cylinder 1006 up into cartridge 206. Moving valve cylinder 1006 up into cartridge 206 creates an opening in cartridge 206 and permits reagent to flow from cartridge 206 through the motorized latch assembly 602 to receiving device 104.

Figure 11B:
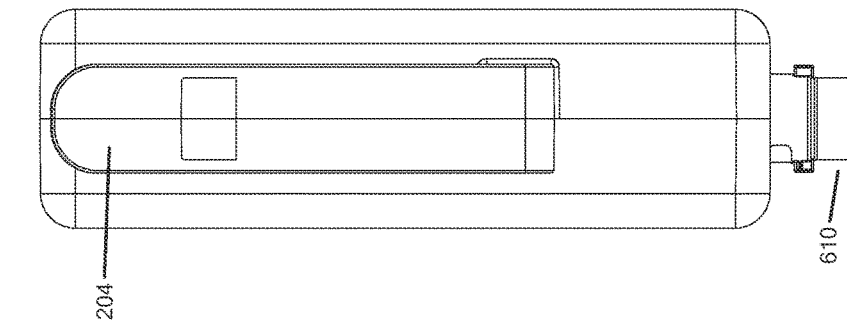
FIG. 11b is a side view of the small cartridge assembly of FIG. 2.
Figure 11A:
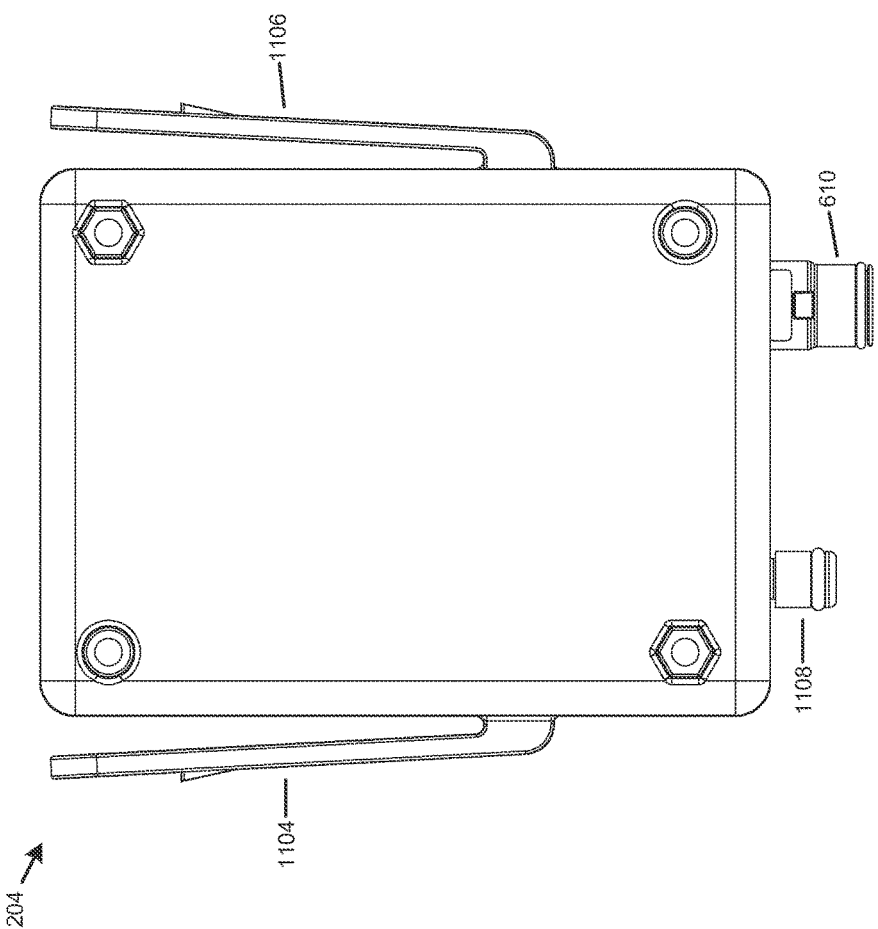
FIG. 11a is a front view of a small cartridge assembly of the reagent magazine assembly of FIG. 2.
Figure 12B:
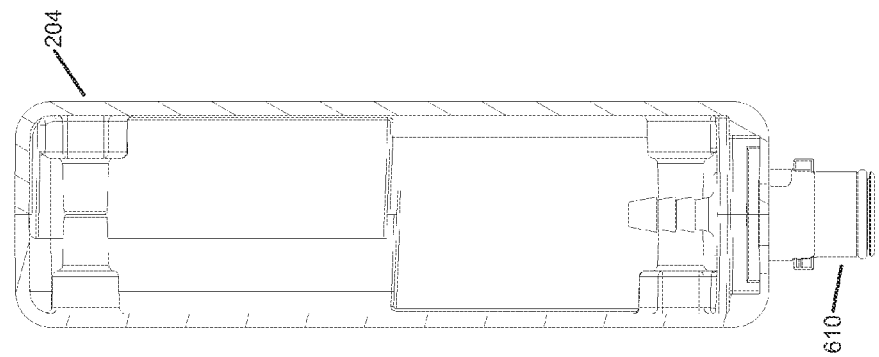
FIG. 12b is a cross-section drawing of the side view of the small cartridge assembly of FIG. 2.
Figure 12A:
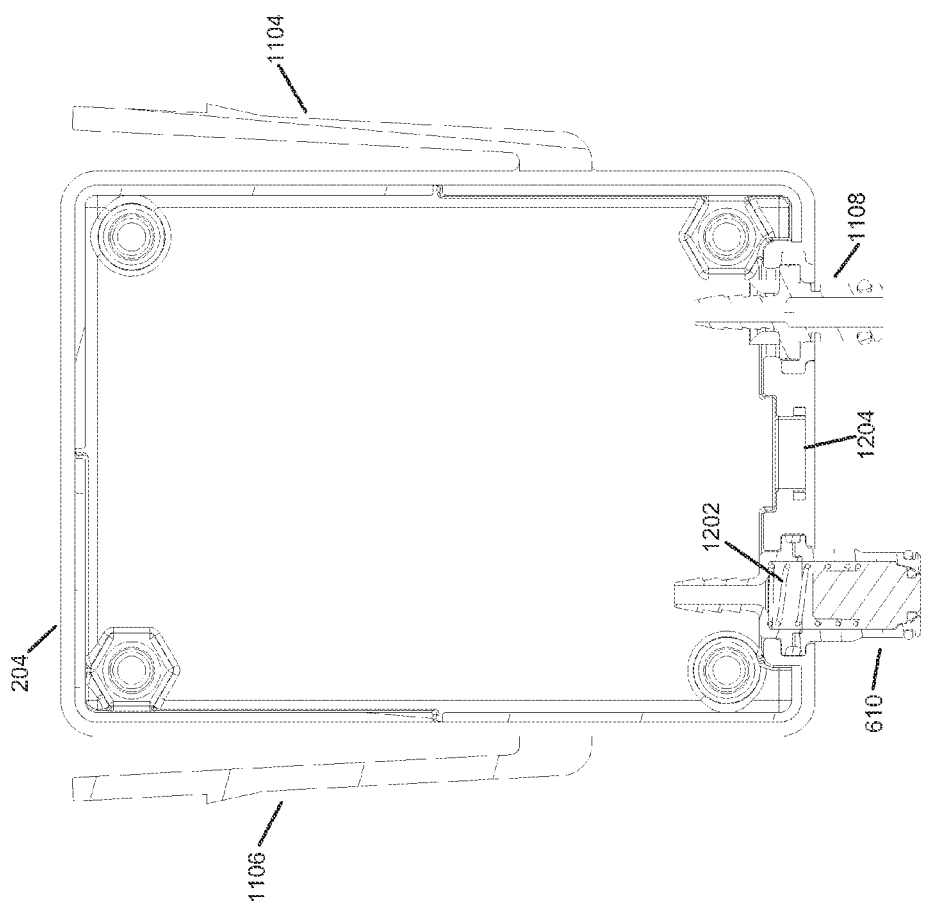
FIG. 12a is a cross-section drawing of the front view of the small cartridge assembly of FIG. 2.
Figure 13:
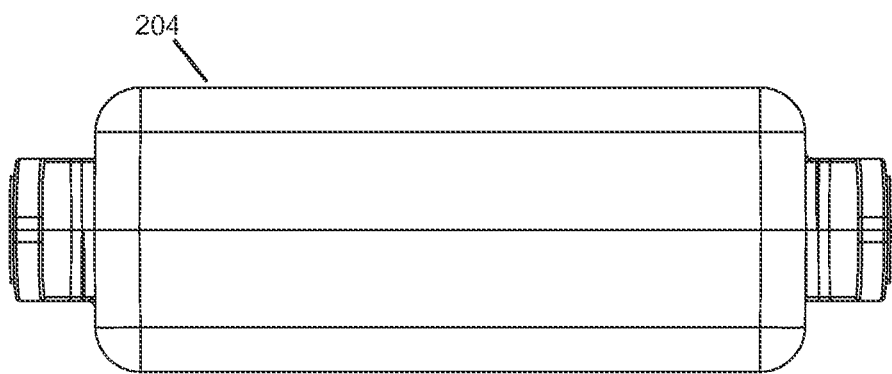
FIG. 13 is a top view of the small cartridge assembly of the reagent magazine assembly of FIG. 2.

FIGS. 11-13 show the cartridge 204. Referring now to FIGS. 11a and 11b, the cartridge 204 includes two detents 1104 and 1106. When cartridge 204 is inserted into magazine assembly 1102, the detents 1104 and 1106 engage rails in the magazine assembly 1102 to lock cartridge 204 in place. To remove the cartridge 204, the detents 1104, 1106 are compressed towards one another until the detents 1104, 1106 clears the rails in the magazine assembly 1102. At that point, the cartridge 204 can be removed.

Cartridge 204 also includes inserts 610 and 1108. Insert 610 connects cartridge 204 to a coupler (not shown) in receiving device 104. In some embodiments, insert 610 may also meter a flow of reagent from cartridge 204 to receiving device 104. Insert 1108 is a make-up insert for air flow out of cartridge 204. When reagent flows out of cartridge 204, a volume within the cartridge 204 is voided. Air is flows through insert 1108 to make up for the volume of reagent that is sucked out of cartridge 204. This air can be sucked into the cartridge 204 to fill the void, or the air can be pressurized to both fill the void and aid in removal of the reagent from the cartridge 204. Inserts 610 and 1108 may connect to separate bladders within cartridge 204.

Referring now to FIGS. 12a and 12b, cross-section views of cartridge 204 are shown. FIG. 12a shows that insert 610 includes a valve 1202. The valve 1202 permits coupling of the reagent from cartridge 204. As shown in FIG. 12a, insert 1108 does not include a valve. However, in some embodiments, insert 1108 may have a valve. In other embodiments, insert 1108 may be a hole covered by a hydrophobic membrane. Both the inserts 1108 and 610 engage structures on the magazine or receiving device, as described previously.

Figure 26:
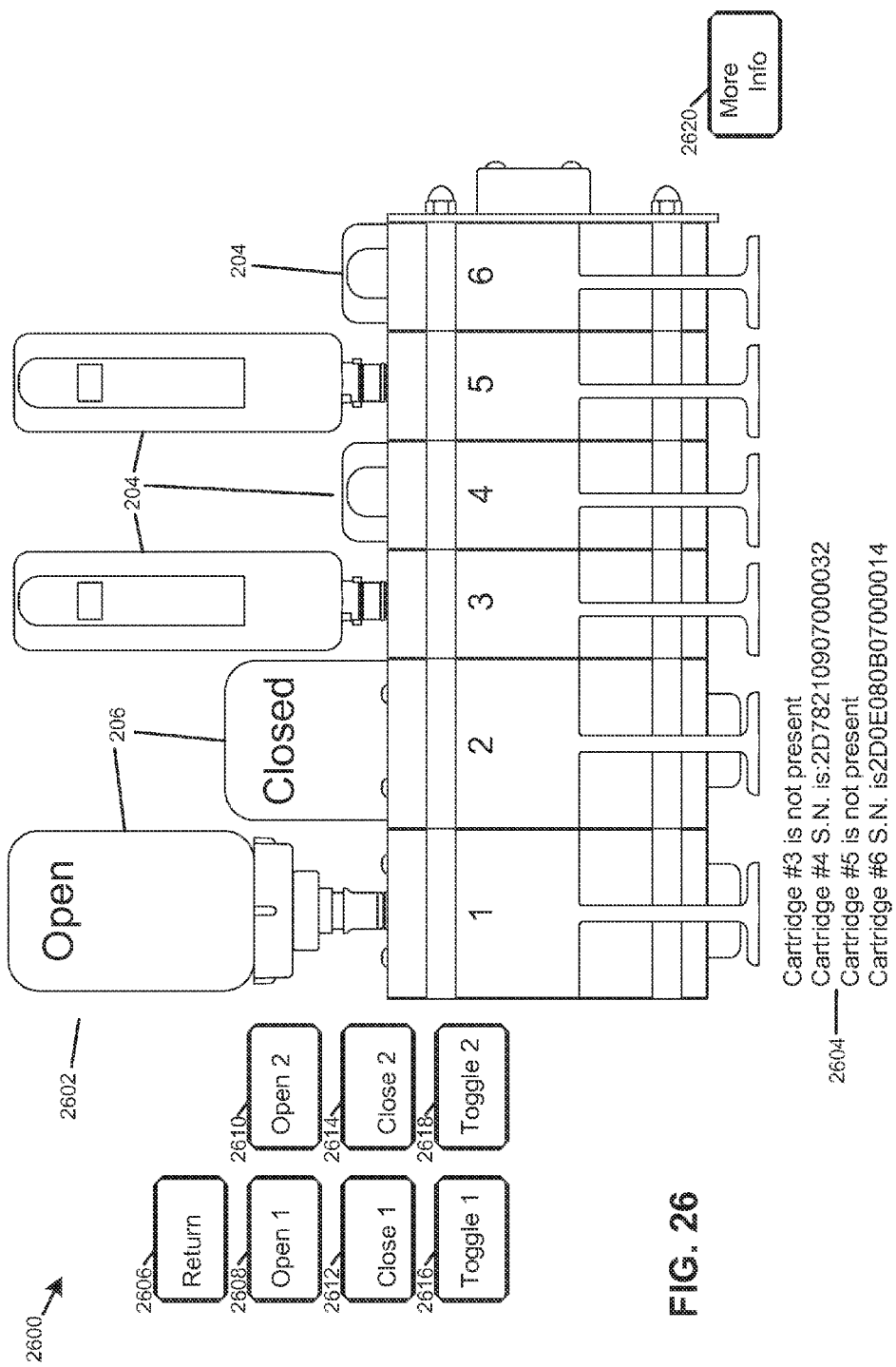
FIG. 26 is an example graphical user interface for the control unit of FIG. 1.

As shown in FIG. 12a, cartridge 204 also includes an electrical connector 1204. When cartridge 204 is inserted into receiving device 104, electrical connector 1204 establishes an electrical connection with another electrical connector (not shown) on receiving device 104. The electrical connection permits identification and other information to be received from cartridge 204 and displayed on GUI 108 of control unit 106. For example, each cartridge typically contains an identifying serial number. When the cartridge is inserted into receiving device 104, the serial number may be displayed on GUI 108, as shown in FIG. 26 and discussed later herein.

In some embodiments, cartridge 204 may include a radio frequency identification (RFID) tag (not shown in FIG. 12a) in lieu of electrical connector 1204. For example, the RFID tag may be embedded on an exterior surface of cartridge 204. In these embodiments, when cartridge 204 is inserted into receiving device 104, an RFID reader device in receiving device 104 reads a serial number for cartridge 204 from the RFID tag. The serial number may then be displayed on GUI 108 of control unit 106. In a similar manner, in some embodiments an RFID tag also may be embedded on an exterior surface of cartridge 206, permitting a serial number from cartridge 206 to be displayed on GUI 108 of control unit 106.

One example of such an RFID system is disclosed in U.S. Pat. No. 6,649,829 filed on May 21, 2002, the entirety of which is hereby incorporated by reference.

In some embodiments, cartridge 204 may include electronics for determining a level of reagent in cartridge 204 and for triggering alarms when the level of reagent is at a high or level threshold. For example, the electronics (not shown in FIG. 12a) may include an ultrasound device, a float mechanism, or other type of level sensor. Other types of information can be obtained from cartridge 204.

Figure 14:
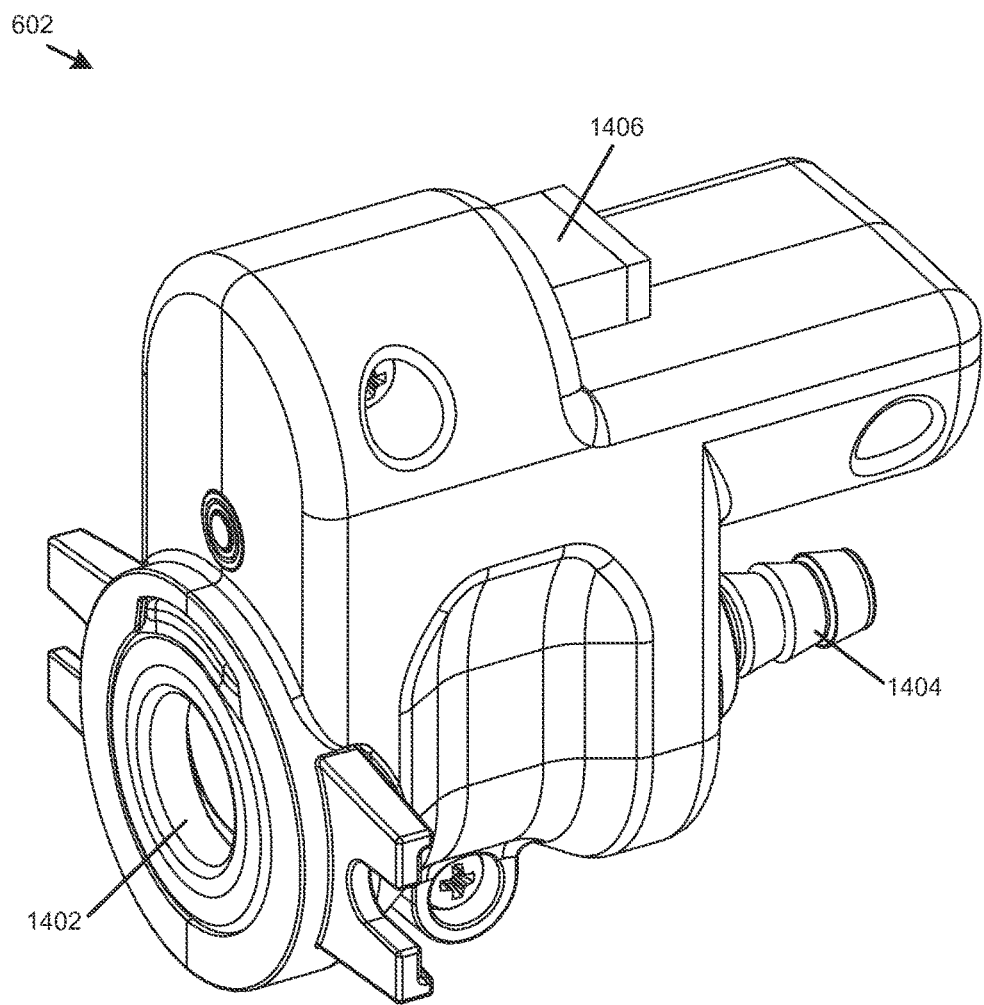
FIG. 14 is a perspective view a motorized latch assembly.
Figure 15:
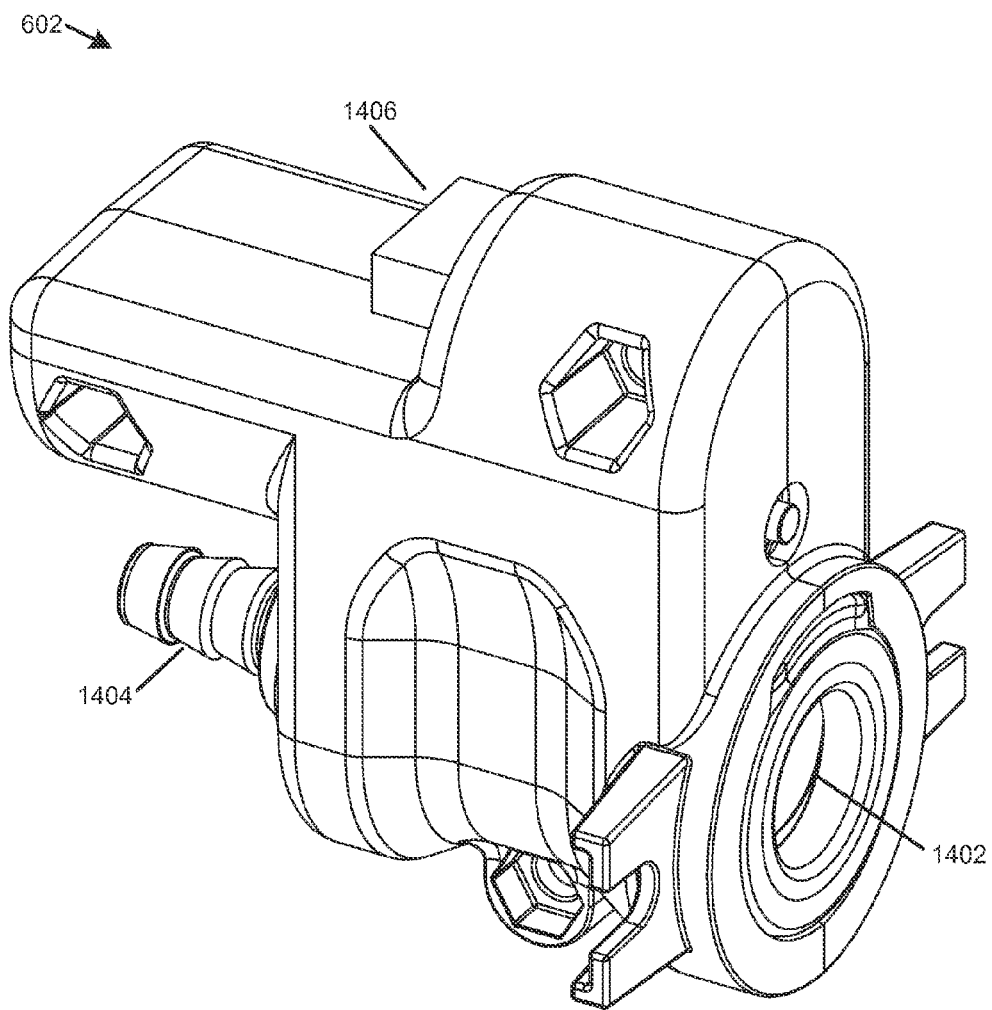
FIG. 15 is another perspective view of the motorized latch assembly of FIG. 14.
Figure 16:
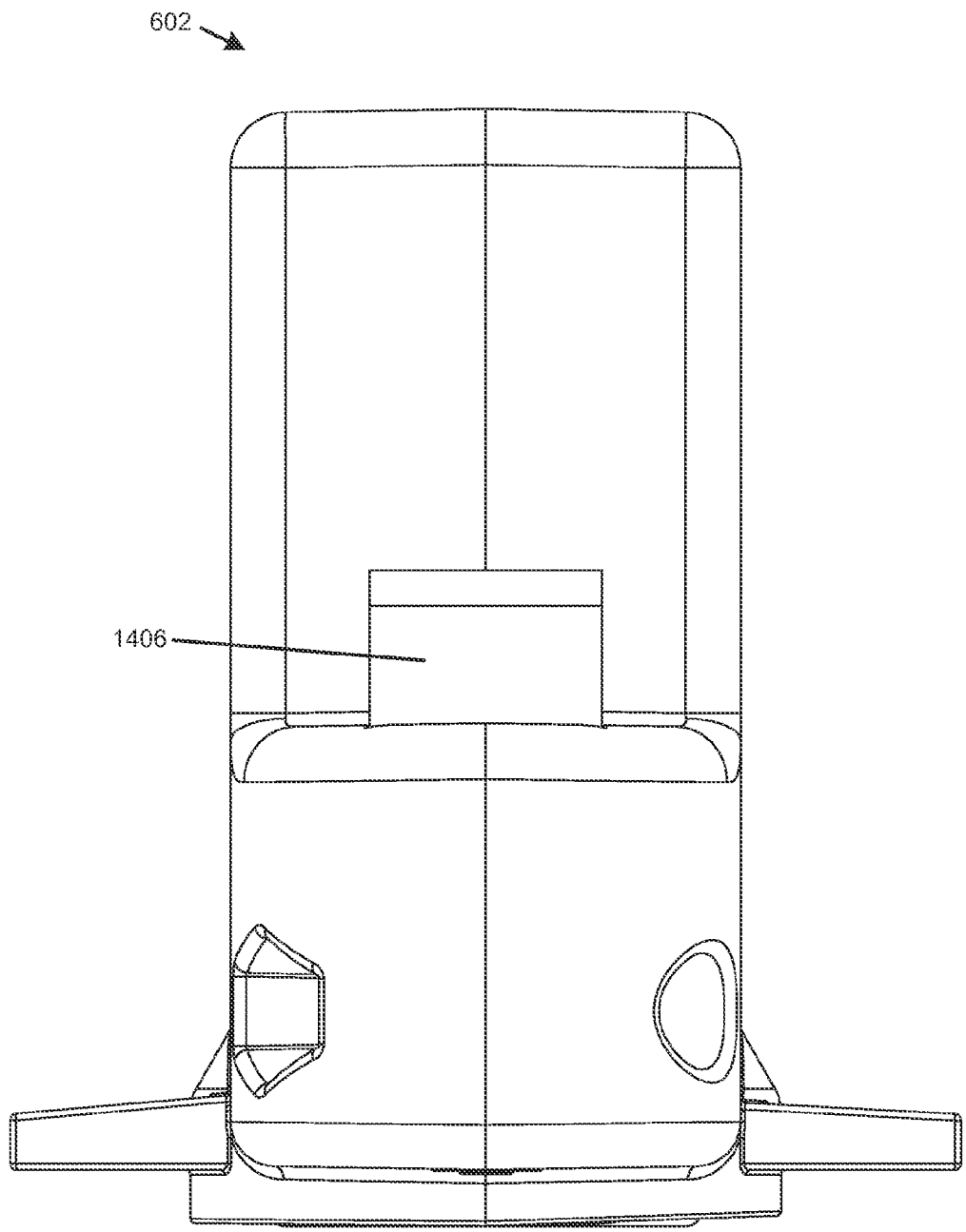
FIG. 16 is a side view of the motorized latch assembly of FIG. 14.
Figure 17:
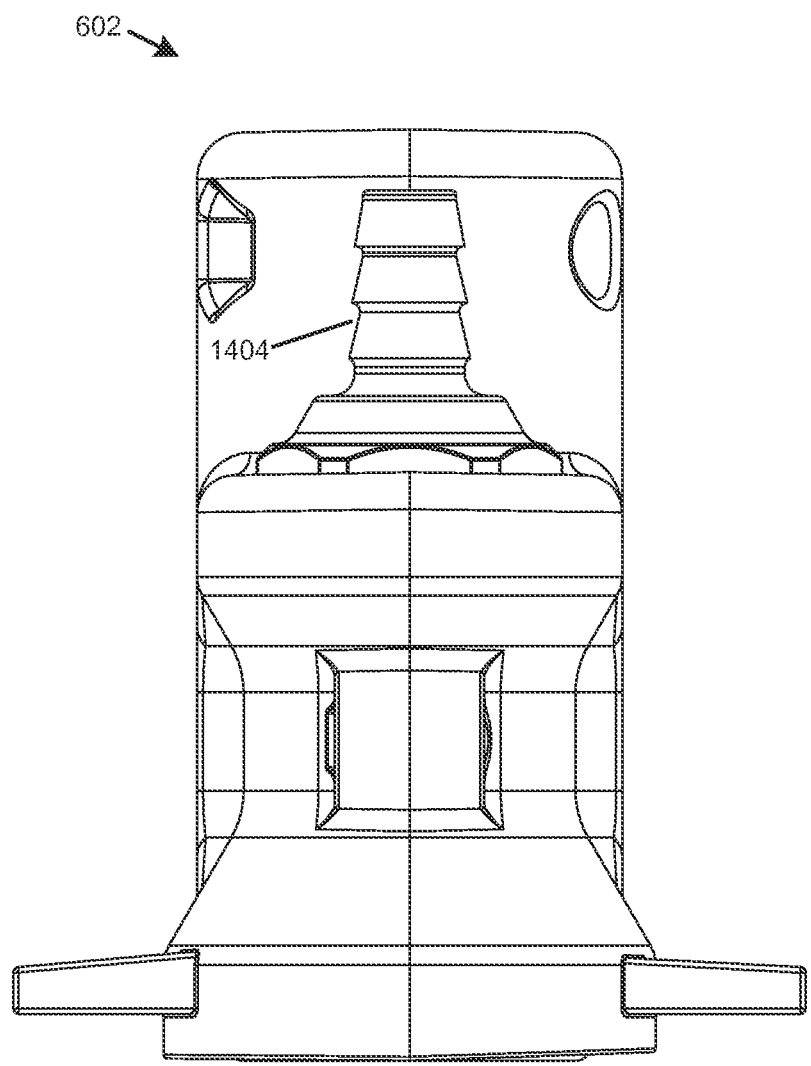
FIG. 17 is a side view of the motorized latch assembly of FIG. 14.
Figure 18:
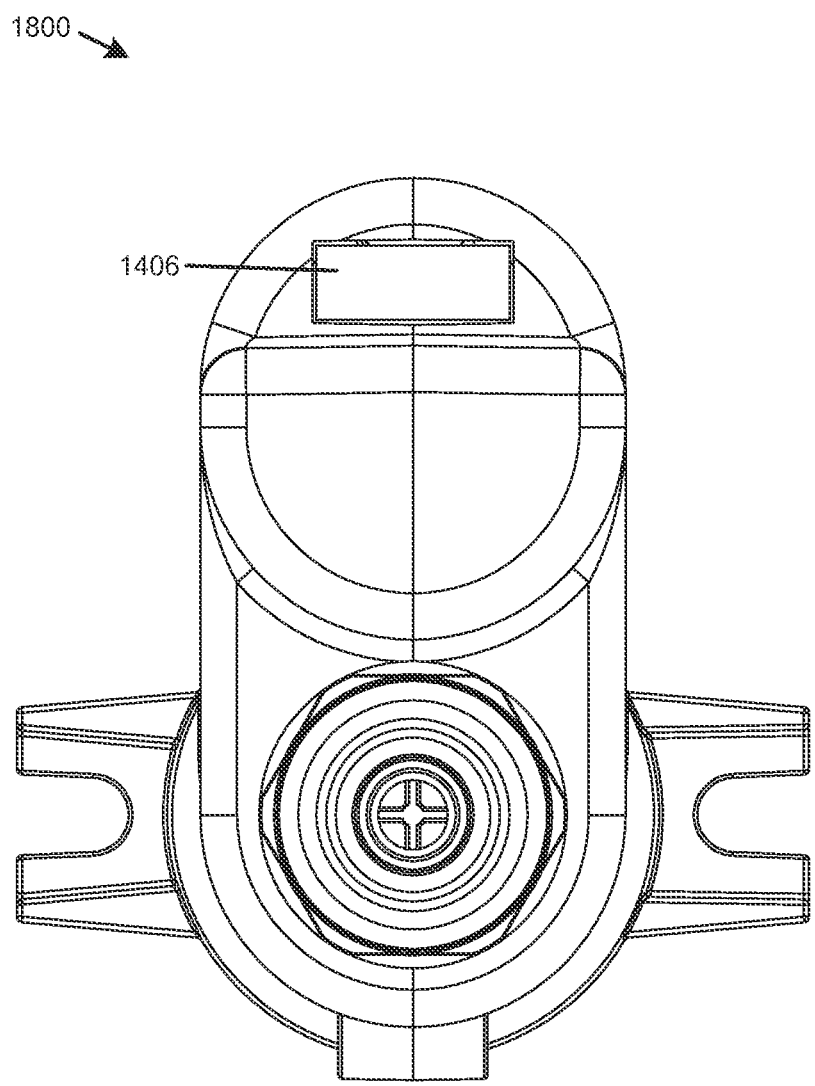
FIG. 18 is a bottom view of the motorized latch assembly of FIG. 14.

Referring to FIGS. 14-18, a perspective view of motorized latch assembly 602 is shown. The motorized latch assembly 602 includes a coupler that couples a cartridge (for example cartridge 206) to the receiving device 104. An insert from the cartridge is connected to the coupler through opening 1402. A hose barb 1404 of the coupler is typically attached to a conduit to move reagent to a desired location in the receiving device 104. FIG. 14 also shows an electrical connector 1406. A hard-wired connection is typically made from the electrical connector 1406 to the control unit 106. Alternately, a wireless connection (for example a Bluetooth connection) may be made from the electrical connector 1406 to control unit 106.

Figure 19:
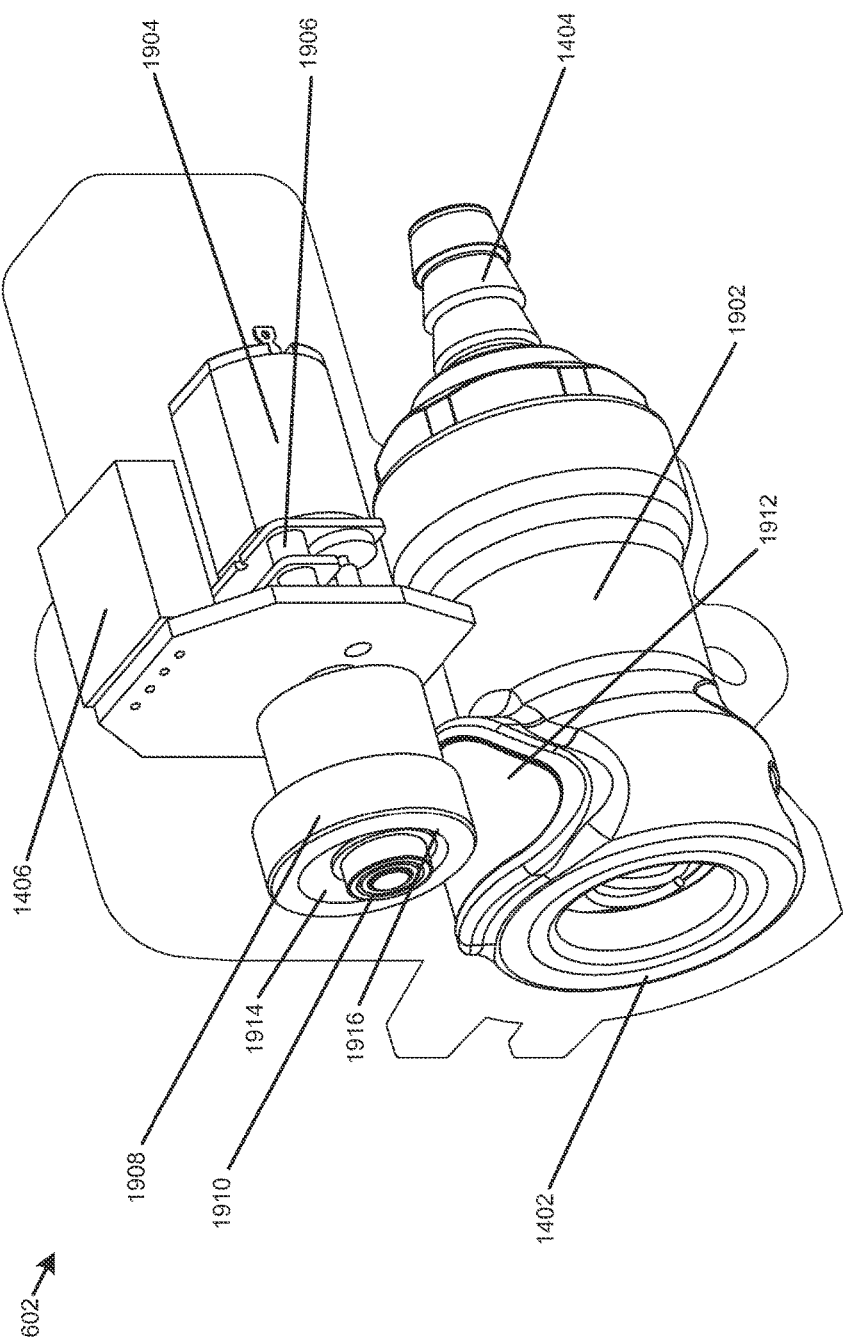
FIG. 19 is another perspective view of the motorized latch assembly of FIG. 14.

Referring now to FIG. 19, another perspective drawing of motorized latch assembly 602 is shown. FIG. 19 shows the coupler 1902 of the motorized latch assembly 602, including the opening 1402 of the coupler 1902 and the hose barb 1404. A motor 1904 is connected via gears 1906 to a rotating eccentric cam 1908. The cam 1908 is offset from a center of cam extension 1910 such that one section 1914 of cam 1908 is longer than another section 1916 that is oriented 180 degrees from section 1914. When the cam rotates, section 1914 makes contact with latch plate 1912, pushing down on latch plate 1912 and opening coupler 1902.

The motor 1904 is activated via control unit 106 via electrical assembly 210. The coupler 1902 is normally in a closed state. When a command is received from control unit 106 to put coupler 1902 in an open state, the motor 1904 is activated. The motor 1904 turns the rotating eccentric cam 1908 via gears 1906. As the rotating eccentric cam 1908 turns, section 1914 of cam 1908 comes in contact with a latch plate 1912 of the coupler 1902, pushing down on latch plate 1912 and opening coupler 1902. When coupler 1902 is opened, cartridge 206 may be physically inserted and locked into coupler 1902.

When a command is received from control unit 106 to put coupler 1902 back into a closed state, the motor rotates cam 1908 further, such that section 1916 of cam 1908 is oriented above latch plate 1912. Because section 1916 is shorter than section 1914, when section 1916 is oriented above latch plate 1912, cam 1908 no longer pushes down on latch plate 1912. When cam 1908 no longer pushes down on latch plate 1912, latch plate 1912 releases back to a closed state, causing cartridge 206 to be locked in coupler 1902.

Figure 20:
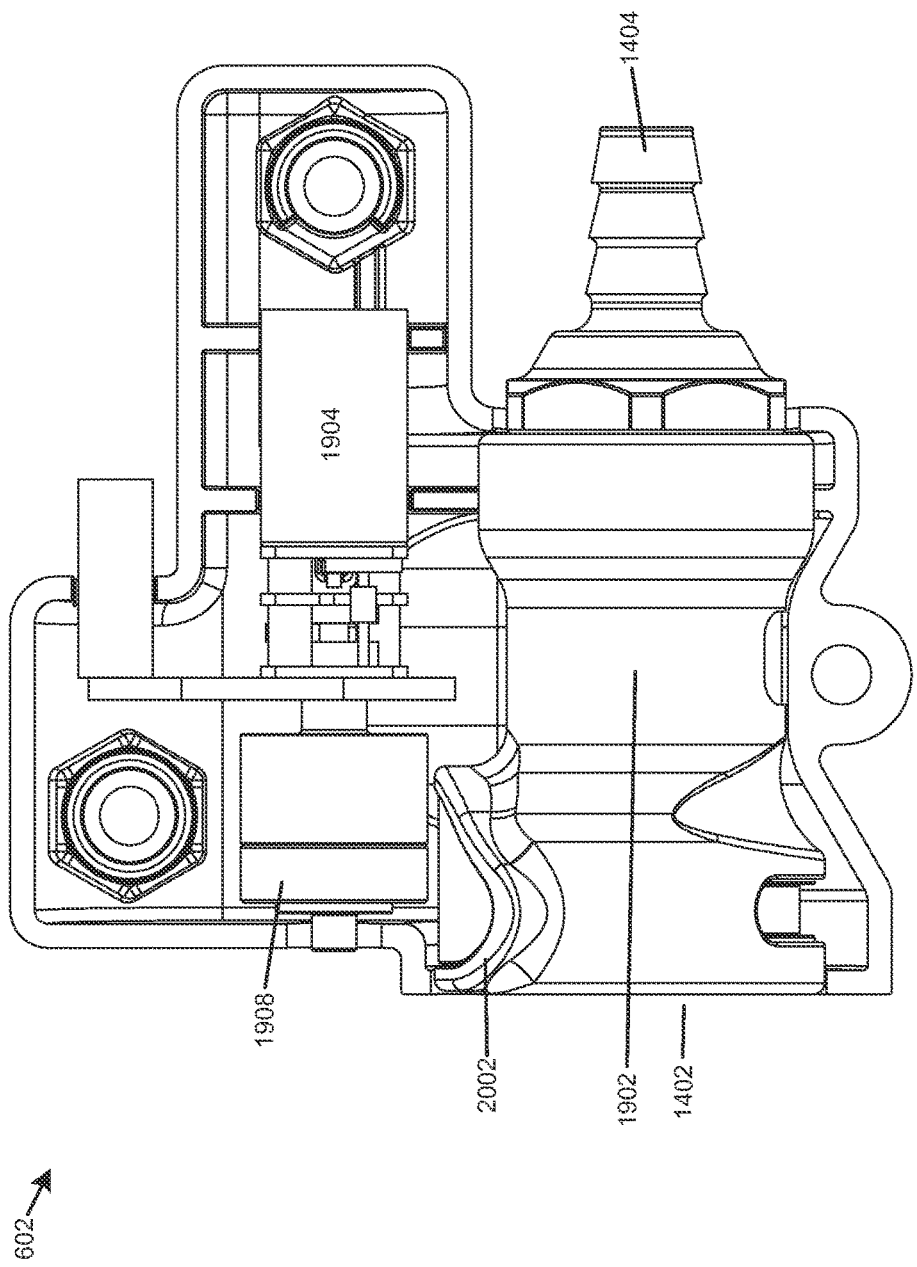
FIG. 20 is a top view of the motorized latch assembly of FIG. 14.
Figure 21:
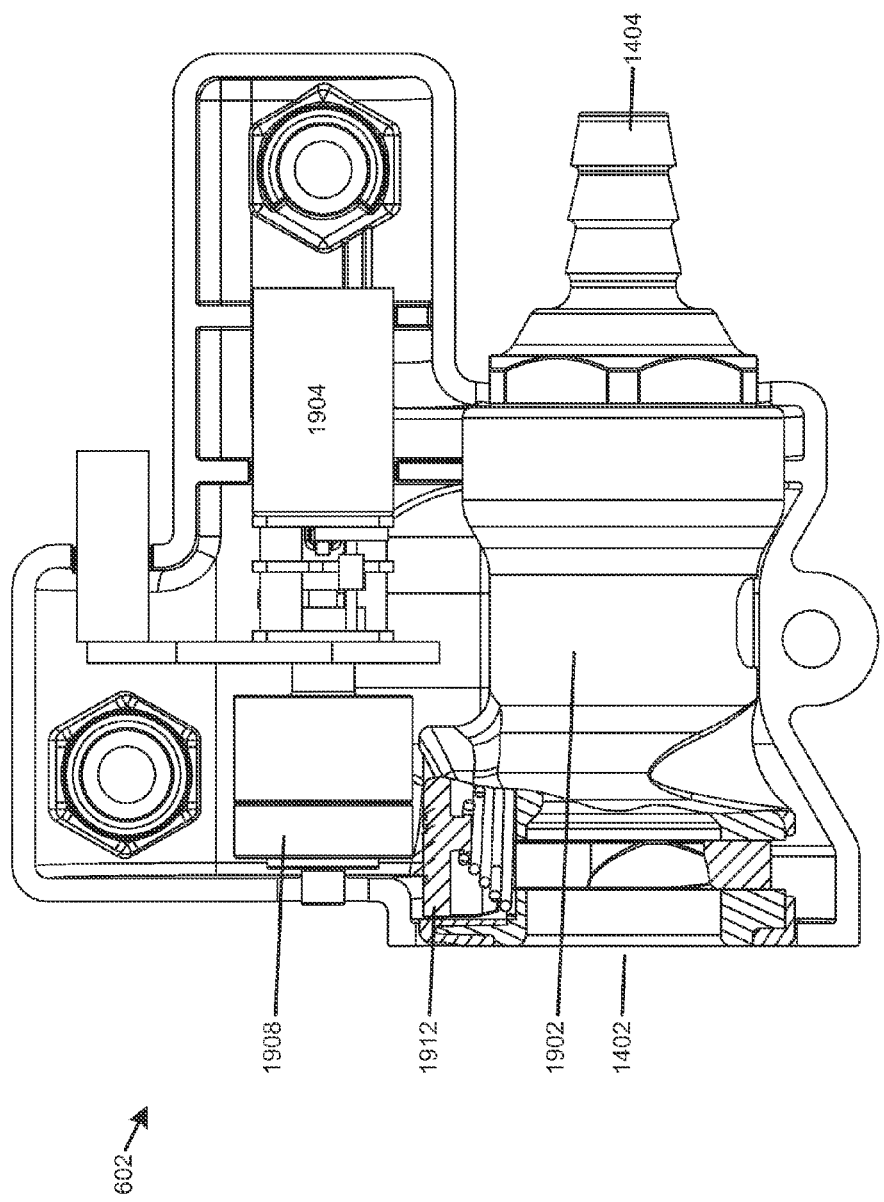
FIG. 21 is a cross-section drawing of the top view of the motorized latch assembly of FIG. 20.
Figure 22:
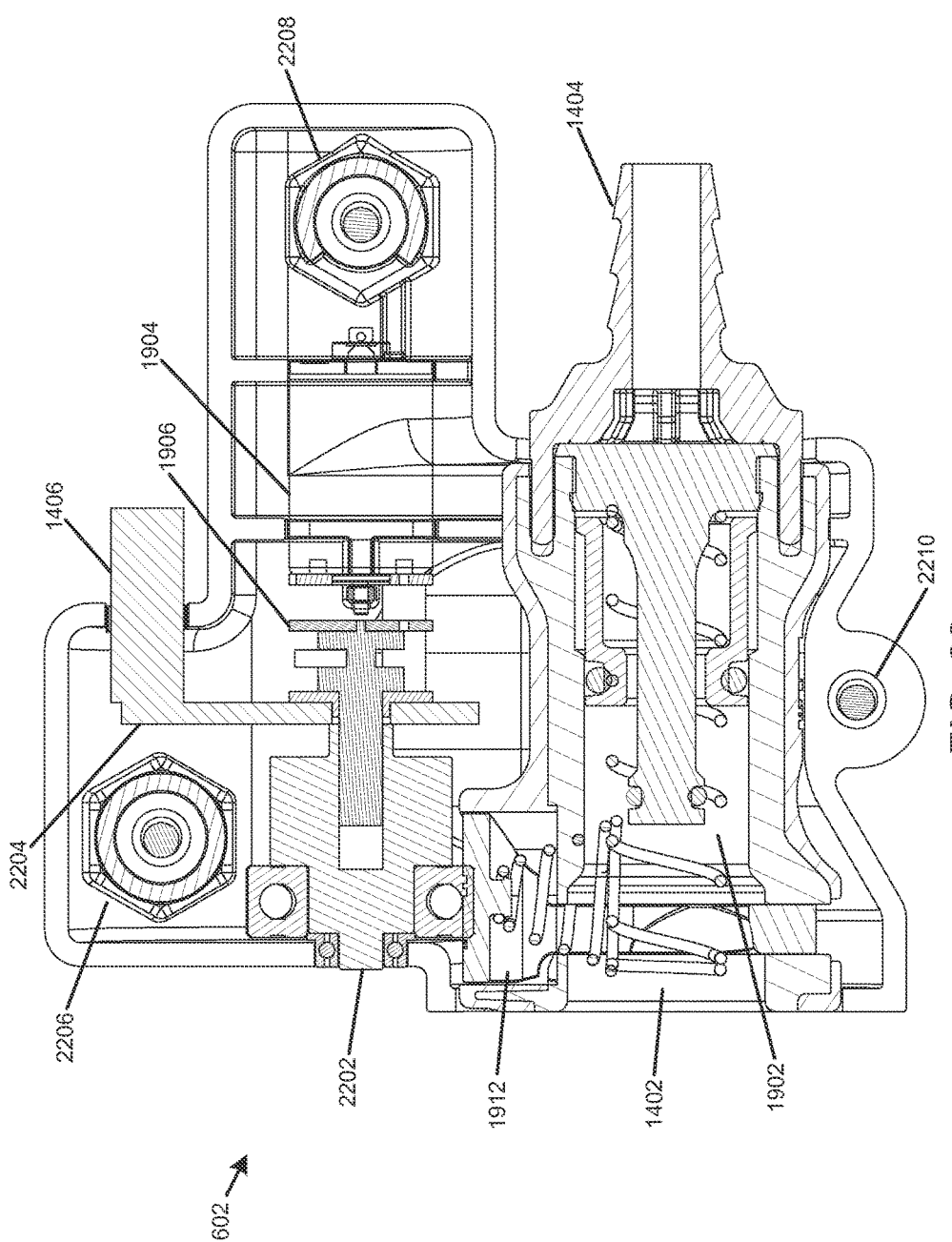
FIG. 22 is another cross-section drawing of the motorized latch assembly of FIG. 14.

Referring now to FIGS. 20-22, the motorized latch assembly 602 is shown in a closed or locked state for the latch plate 1912. FIG. 20 shows the top 1402 of the coupler 1902 and the hose barb 1404 of the coupler 1902. Also shown are the motor 1904 and the cam 1908. As shown in FIG. 20, the cam 1908 is not pressing downward on latch plate 1912 (covered by shroud 2002) and therefore coupler 1902 is in a closed state. As shown in FIG. 21, cam 1908 is not making contact with latch plate 1912.

FIG. 22 shows the opening 1402 of the coupler 1902 and the hose barb 1404 of the coupler 1902. Also shown are the motor 1904, the gears 1906 and the eccentric cam and cam extension 2202. The motorized latch assembly 602 also includes a printed circuit board 2204. The printed circuit board 2204 includes wiring from the electrical connector 1406 to the motor 1904. Also shown in FIG. 22 are the latch plate 1912 and fasteners 2206, 2208 and 2210.

The motorized latch assembly 602 is shown in a closed position. In the closed position, the latch plate 1912 covers part of the opening 1402 of the coupler 1902, preventing a cartridge that is inserted and locked in coupler 1902 from being removed from coupler 1902.

When a command to open coupler 1902 is received from control unit 106, the motor 1904 rotates the eccentric cam 2202. As the eccentric cam 2202 rotates, the eccentric cam 2202 presses down against latch plate 1912, causing latch plate 1912 to move away from the opening 1402 of the coupler 1902. When latch plate 1912 moves away from the opening 1402 of the coupler 1902, the opening 1402 of the coupler 1902 becomes larger, permitting the cartridge 206 to be inserted into coupler 1902 or removed from coupler 1902.

Figure 23:
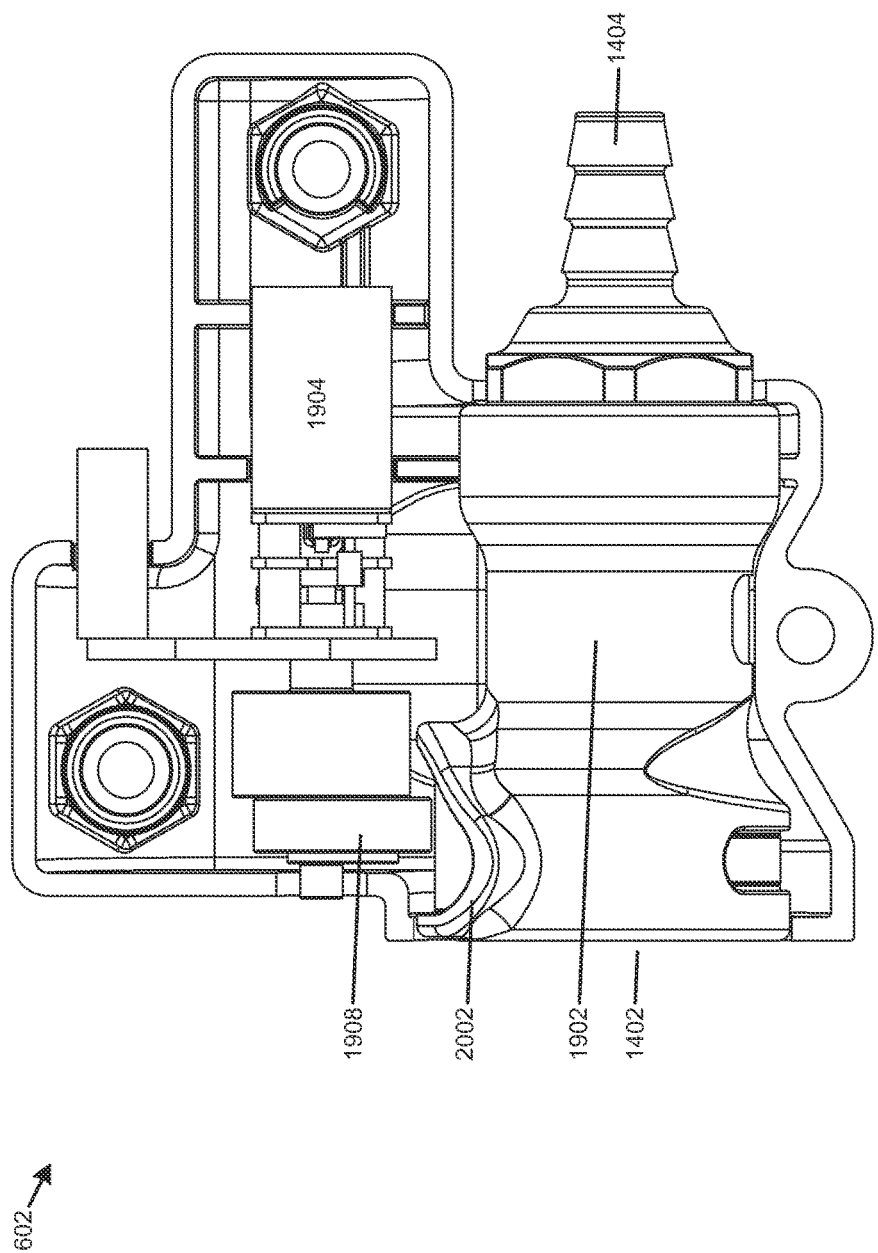
FIG. 23 is another top view of the motorized latch assembly of FIG. 14.
Figure 24:
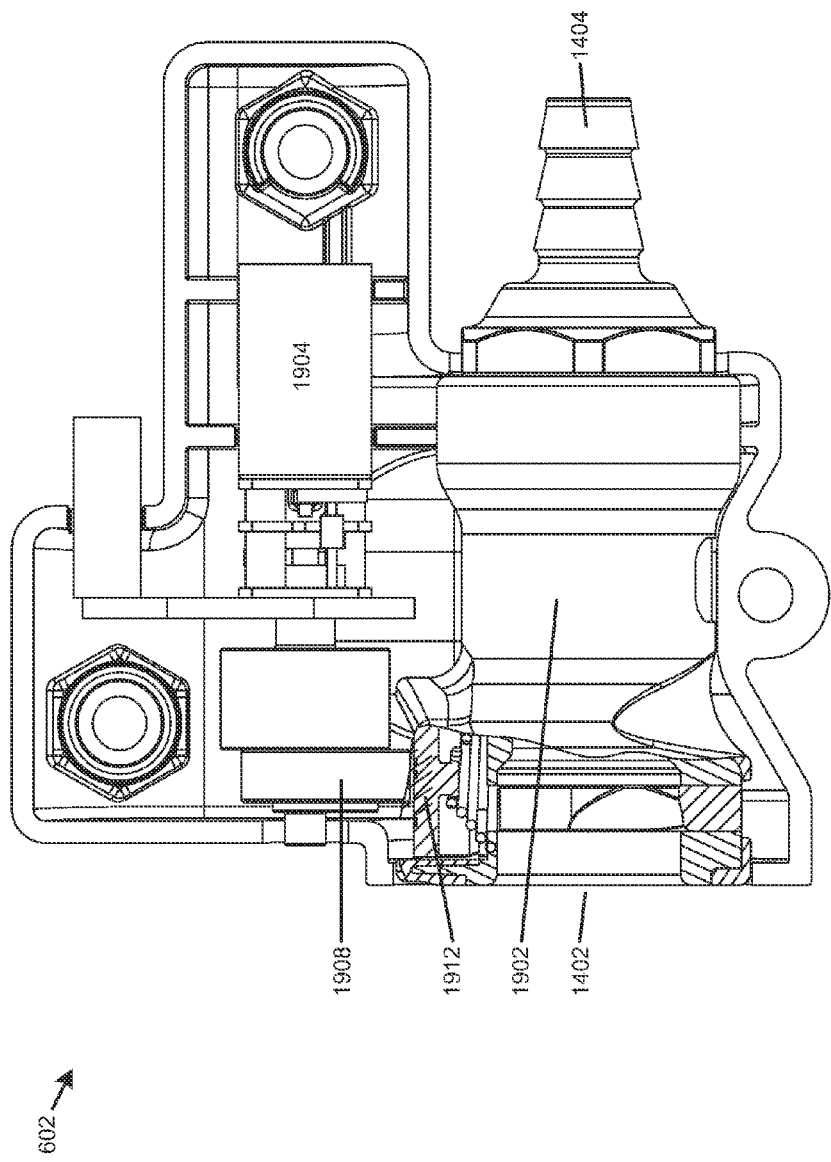
FIG. 24 is a cross-section drawing of the top view of the motorized latch assembly of FIG. 23.
Figure 25:
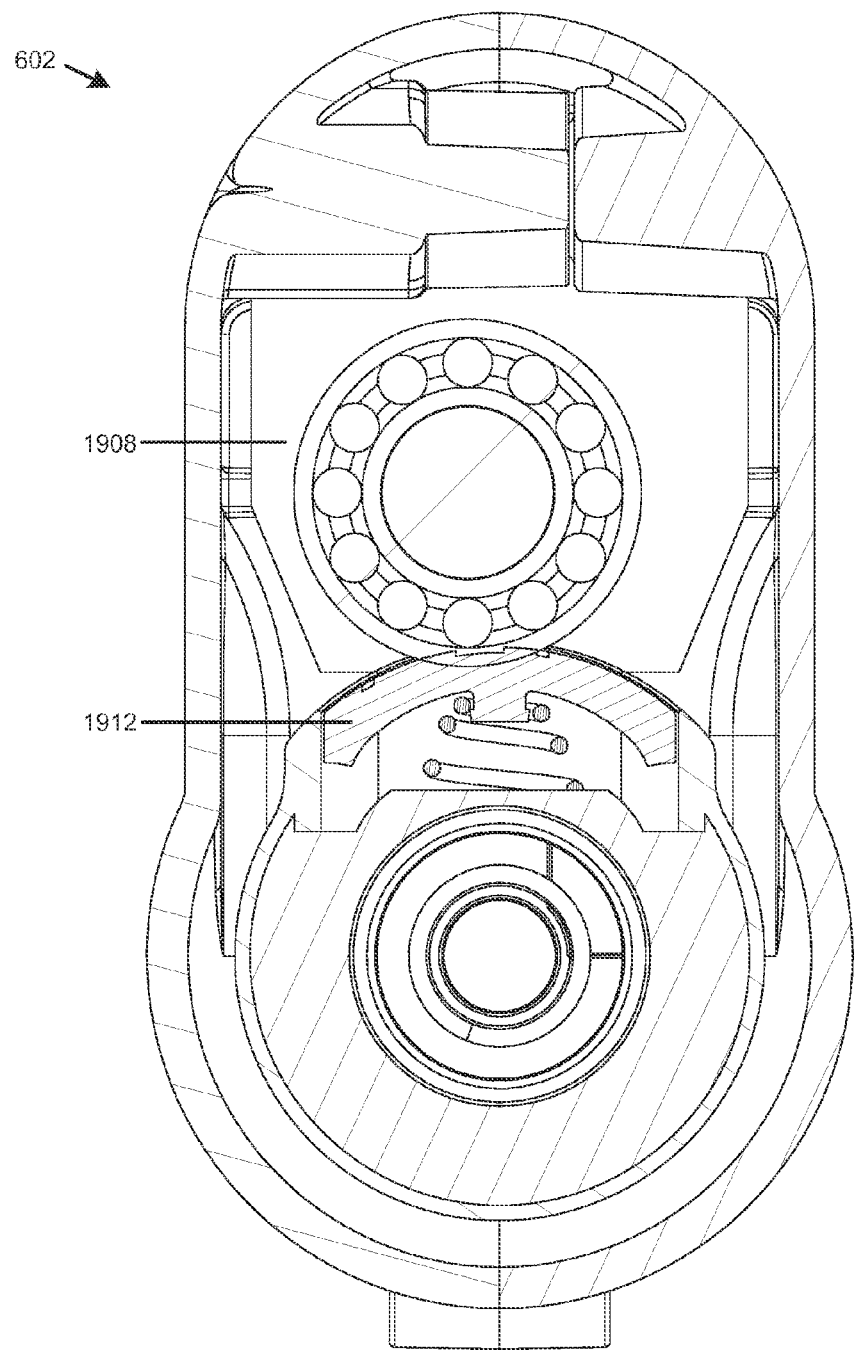
FIG. 25 is another cross-section drawing of the motorized latch assembly of FIG. 14.

Referring now to FIGS. 23-25, the motorized latch assembly is shown with the coupler in the open position. FIG. 23 shows cam 1908 rotated so that cam 1908 presses down on latch plate 1912 (covered by shroud 2002). Now referring to FIG. 24, cam 1908 is shown pressing down on latch plate 1912, thereby opening coupler 1902 and permitting the insert 1002 of the cartridge 206 to be inserted into coupler 1902 or removed from coupler 1902.

Now referring to FIG. 26, an example graphical user interface (GUI) 2600 for control unit 106 is shown. The example GUI shows an illustration 2602 of the reagent magazine assembly 102. As shown, the reagent magazine assembly includes two cartridges 206, labeled 1 and 2 respectively, and four cartridges 204, labeled 3-6 respectively. Cartridges 1, 3 and 5 are shown as being disconnected and cartridges 2, 4 and 6 are shown as being connected. With regard to FIG. 26, a disconnected cartridge (labeled Open in FIG. 26) refers to a cartridge that is not inserted into a coupler on motorized latch assembly 602 and a connected cartridge (labeled Closed in FIG. 26) refers to a cartridge that is inserted and locked into the coupler on motorized latch assembly 602.

Identification information 2604 is also shown for these cartridges. For cartridges 3-6, serial numbers are shown for the cartridges that are in a connected position—namely cartridges 4 and 6. Serial numbers are not shown for the cartridges that are in a disconnected position. Instead, a not present message is displayed. This is because the cartridges need to be inserted in the reagent magazine assembly 102 in order for electronics included within the reagent magazine assembly 102 to read to the serial numbers for these cartridges.

As discussed earlier herein with regard to electrical connector 1204, the electronics may comprise one or more integrated circuits (ICs) that are included in cartridge 204 and also in receiving device 104. The electronics can automatically control the opening and closing of the latch plate to permit insertion and removal of cartridges. The electronics may incorporate Bluetooth or other similar technology to permit remote opening and closing of the latch plate. The electronics may also be able to identify fluid levels in the cartridges. Other uses for the electronics are possible. In lieu or in addition to ICs, cartridges 204 and 206 may include RFID tags that are read by an RFID reader device in receiving device 104 to obtain an identifying serial numbers from cartridges 204 and 206.

The GUI 2600 also provides command buttons 2606-2620 for initiating operations on the reagent magazine assembly 102. The example command buttons include button 2608 for opening a coupler for cartridge 1, button 2610 for opening a coupler for cartridge 2, button 2612 for closing the coupler for cartridge 1, button 2614 for closing the coupler for cartridge 2, button 2616 for toggling the coupler for cartridge 1 from a disconnected state to a connected state or from a connected state to a disconnected state and button 2618 for toggling the coupler for cartridge 2 from a disconnected state to a connected state or from a connected state to a disconnected state. Opening a coupler refers to putting a coupler of motorized latch assembly 602 in disconnected state wherein the cartridge may be physically connected through the coupler of motorized latch assembly 602 to a coupler in the body of receiving device 104 or the cartridge may be removed from the coupler of motorized latch assembly 602; closing a cartridge refers to putting the coupler of motorized latch assembly 602 in a connected state wherein the latch plate is returned to a closed position and the cartridge is locked in place and prevented from being removed from the coupler of the motorized latch assembly 602.

The GUI 2600 also includes a More Info button 2620 and a Return button 2606. The More Info button 2620 brings up another user interface screen (not shown) that provides additional information regarding the system 100. For example, when cartridges 3-6 include motorized latch assemblies, the additional information may include control buttons for cartridges 3-6. In example embodiments, the additional information may also include a display or an indication of the levels of reagent in each of the cartridges. In example embodiments, users may have the ability to set alarm thresholds for the levels of reagent in each cartridge, for example high-level alarms and low-level alarms. In example embodiments, maintenance information may be provided regarding the cartridges and other aspects of the system 100. Other types of information are possible.

The Return button 2606 causes a return to a previous user interface screen, for example a home screen. For example, the home screen may display information regarding a plurality of other systems and permit a user to select a system to display a user interface screen similar to GUI 2600.

Figure 27:
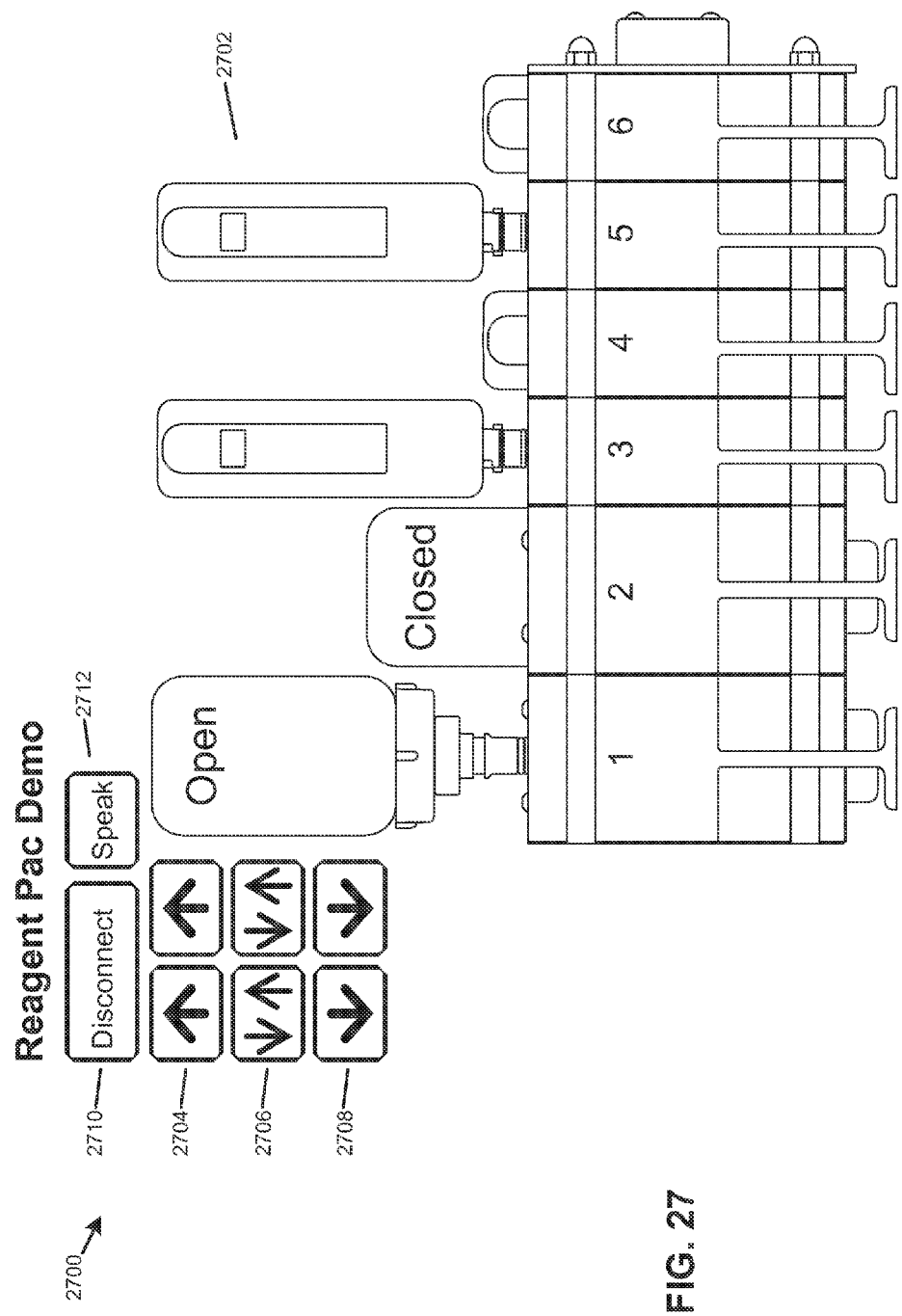
FIG. 27 is another graphical user interface for the control unit of FIG. 1.

Now referring to FIG. 27, another example GUI 2700 for control unit 106 is shown. In an example embodiment, GUI 2700 may be part of a software application on a mobile device such as a smart telephone or a tablet computer. Displaying a GUI of the system 100 on a smart telephone or a tablet computer permits a user to monitor and control the system 100 remotely. In some embodiments, the smart telephone or tablet computer may connect to the system 100 using a wireless technology such as Bluetooth. In other embodiments, a cellular telephone connection may be used.

The example GUI 2700 includes a visual display 2702 of the cartridges and reagent magazine of the system 100. Also included are open buttons 2704, indicated by upward pointing arrows, toggle buttons 2706, indicated by arrows pointing both upward and downward and close buttons 2708, indicated by downward pointing arrows. The open buttons 2704 are used to put couplers for cartridges 1 and 2 into a disconnected state. The close buttons 2708 are used to put couplers for cartridges 1 and 2 into a connected (locked) state. The toggle buttons 2706 are used to toggle cartridges 1 and 2 between disconnected and connected states. As indicated earlier herein, when a coupler is in a connected state, a cartridge is prevented from being removed from a coupler in motorized latch assembly 602. Similarly, when a coupler is in a disconnected state, a cartridge is enabled to be inserted into the coupler in the motorized latch assembly 602. Also, as discussed earlier herein, in some embodiments a cartridge may be inserted in the coupler in the motorized latch assembly 602 while in a connected state. However, the cartridge cannot be removed from the coupler while in the connected (locked) state, The example GUI 2700 are includes a Disconnect button 2710 and a Speak button 2712. The example Disconnect button 2710 disconnects the wireless or cellular connection to the system 100. The example Speak button 2712 permits the user to issue voice commands to GUI 2700. For example, the voice commands may be used to connect and disconnect cartridges, display information, set alarms, etc.

Figure 28:
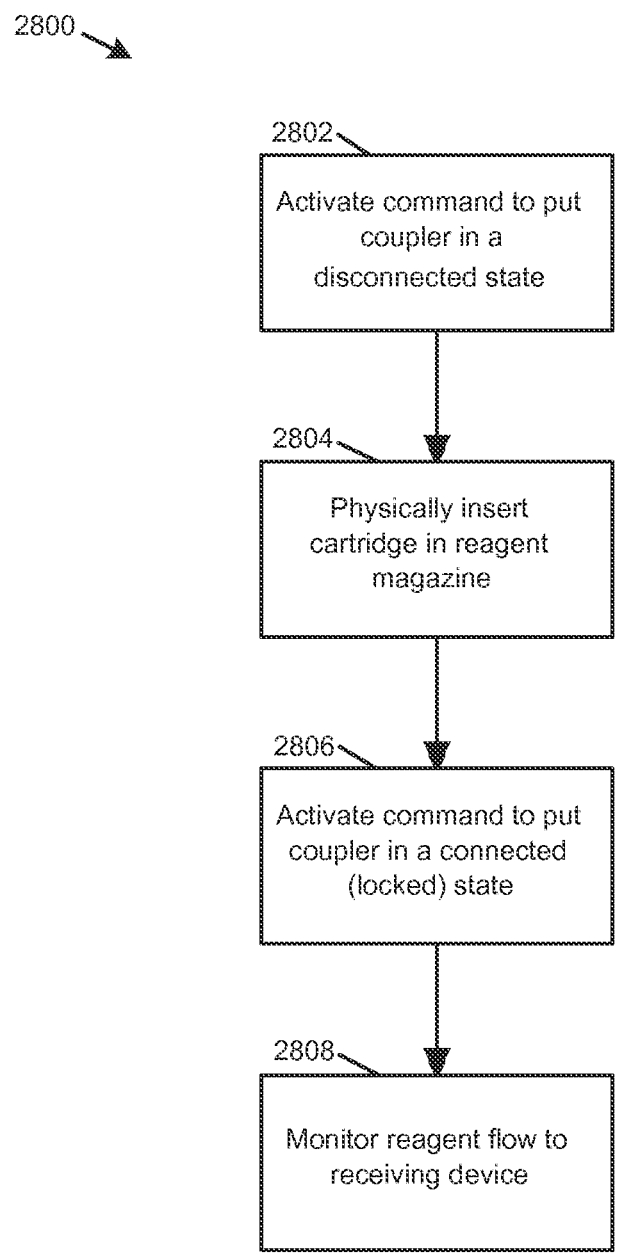
FIG. 28 is a flow chart for a method for physically connecting a cartridge to a receiving device using a motorized latch.

Referring to now to FIG. 28, an example method 2800 for physically connecting a cartridge to a receiving device is shown. In this example method, the cartridge is cartridge 206 of system 100. At operation 2802, a command is activated to put a coupler for cartridge 206 in a disconnected state. The command is typically activated at a GUI of control unit 106, for example by selecting Open 1 button 2608 on GUI 2600. Alternatively, the command may be activated remotely, for example via GUI 2700 on a smart telephone or tablet computer software application.

When the command is activated, a latch plate on motorized latch assembly 602 is pushed down, permitting cartridge 206 to enter the coupler for cartridge 206 on motorized latch assembly 602. For example, the motorized latch causes cam 1908 to press down on latch plate 1912, permitting cartridge 206 to fit through an opening 1402 of coupler 1902 and become physically connected to coupler 1902.

At operation 2804, cartridge 206 is physically inserted into reagent magazine assembly 102. The cartridge 206 is inserted through coupler 1902 of motorized latch assembly 602 so that the cartridge becomes physically connected to the coupler and so that a flow path exists between cartridge 206 and receiving device 104.

At operation 2806, a command is activated to put the coupler for cartridge 206 in a connected (locked) state. When the command is activated, the latch plate on motorized latch assembly 602 is released, locking cartridge 206 in the coupler of motorized latch assembly 602.

When cartridge 206 is inserted into the coupler in the body of receiving device 104, a valve in coupler 1902 is pushed open, causing reagent to flow from cartridge 206 to receiving device 104. At operation 2808, reagent flow to receiving device 104 may be monitored. For example, a metering device may be included in cartridge 206 or in reagent magazine assembly 102 to monitor the reagent flow.

Figure 29:
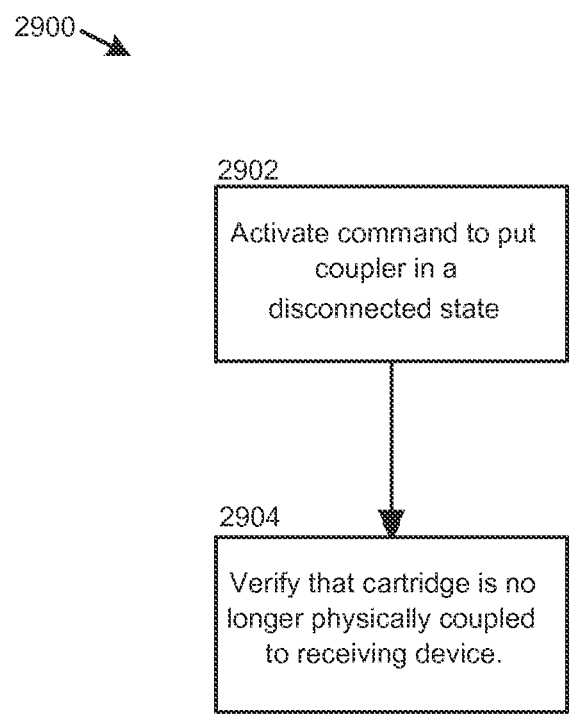
FIG. 29 is a flow chart for a method for disconnecting a cartridge from a receiving device using a motorized latch.

Referring to now to FIG. 29, an example method 2900 for disconnecting a cartridge from a receiving device is shown. In this example method, the cartridge is cartridge 206 of system 100. At operation 2902, a command is activated to put the coupler for cartridge 206 in a disconnected state. For example the command may be an open command. In some embodiments the open command may be activated from a GUI on a display screen on control unit 106. In other embodiments the open command may be activated from a software application on a smart telephone or tablet computer.

When the cartridge 206 is in the disconnected state, a latch plate on motorized latch assembly 602 is released, unlocking cartridge 206 and permitting cartridge 206 to be removed from the coupler of motorized latch assembly 602. In some embodiments when the latch plate is released, a spring-biased valving mechanism in the motorized latch assembly 602 causes cartridge 206 to disconnect from a coupler in the motorized latch assembly 602. In other embodiments where the coupler of motorized latch assembly 206 does not have a valving mechanism, cartridge 206 needs to be manually removed from the coupler. When cartridge 206 is disconnected from the coupler, cartridge 206 is no longer physically connected to the coupler and the flow path between cartridge 206 and receiving device 104 is broken. At operation 2904, a verification is made that cartridge 206 is no longer physically coupled to receiving device 104.

Figure 30:
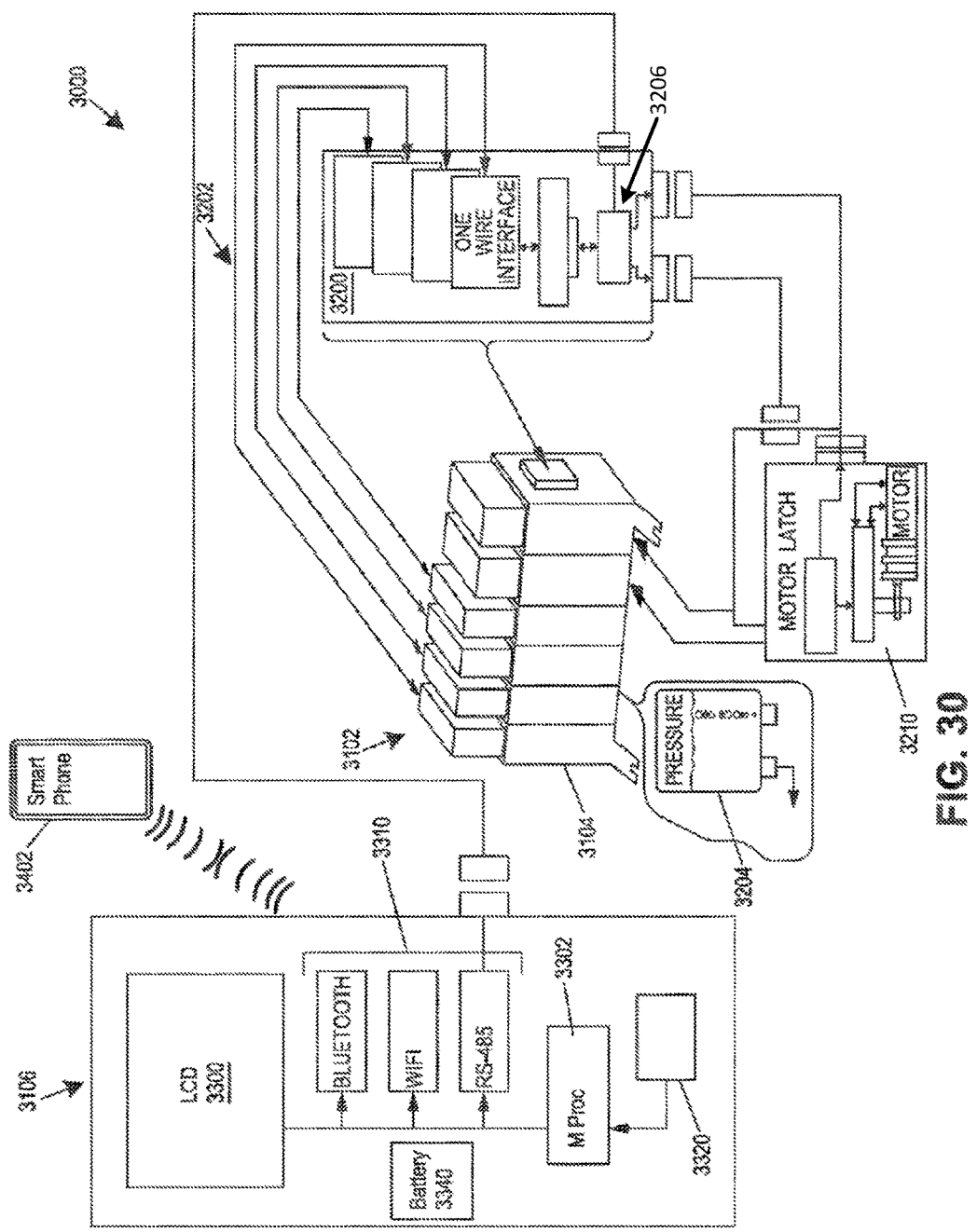
FIG. 30 is a block diagram of another example system that includes a reagent magazine and a motorized latch coupler.

Referring now to FIG. 30, another example system 3000 is shown. The system 3000 is similar to the system 100 described above, in that the system 3000 includes a reagent magazine assembly 3102, a receiving device 3104, a control unit 3106.

The reagent magazine assembly 3102 includes one or more cartridges 3204 that house a liquid and/or gas. In some examples, the cartridges 3204 include one or more bladders for holding the liquid or gas and one or more ports for dispensing the liquid or gas and/or for providing access for a pressurized gas to assist in dispensing, such as makeup air. In other examples, the cartridges 3204 can be sealed such that no bladders are needed within the cartridges 3204, since the cartridge itself can retain the liquid. Each of the cartridges Each of the cartridges communicates, in the example shown, over a dedicated wire 3202 with a control unit 3200 on the receiving device 3104.

The control unit 3200 of the receiving device 3104 includes a microprocessor that controls the receiving device 3104 and communications with the cartridges 3204 and motorized latches 3210. In this example, the control unit 3200 includes a hub 3206 and communicates with each of the motorized latches 3210 on the receiving device 3104 using an interface such as RS-485. In this manner, the control unit 3200 controls the state (i.e., open or closed) for each of the motorized latches 3210 on the receiving device 3104.

The control unit 3106 can include a display 3300, a microprocessor 3302, and one or more communication modules 3310. The display 3300 can be an LCD or similar type of display for showing a graphical user interface (e.g., FIGS. 26-27). The microprocessor communicates with the display 3300 and communication modules 3310 to control them.

In some examples, the control unit 3106 is powered by a battery 3340 that allows the control unit 3106 to be plugged into the control unit 3200 and control the same without requiring a wired source of power.

The communication modules 3310 allow the control unit 3106 to communicate through wired and/or wireless interfaces with other devices. For example, the control unit 3106 communicates with the control unit 3200 to control the receiving device 3104. In this example, the control unit 3106 uses a wired interface for communication.

In addition, the communication modules 3310 support wireless interfaces, such as WiFi and/or Bluetooth. In this example, the communication modules 3310 support wireless communications with a separate controller 3402, such as a smartphone or other computer. As described further above, the separate controller 3402 can include one or more applications configured to communicate with the control unit 3106 to control the system 3000.

In one example, the control unit 3106 also includes memory 3320, such as a flash EEPROM. The memory 3320 can be programmed to control the control unit 3106. In this example, a program can be stored on the memory 3320 that is used to control the control unit 3106. The program can be loaded onto the memory 3320 and read by the microprocessor 3302 of the control unit 3106 during execution.

Additional details about alternative systems, including those with motorized latches, are described in U.S. Patent Application Ser. No. 62/037,395 filed on Aug. 14, 2014, the entirety of which is hereby incorporated by reference.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A system, comprising:
    a receiving device;
    a fluid cartridge magazine assembly coupled to the receiving device and configured to releasably receive at least one fluid cartridge, the fluid cartridge magazine assembly comprising:
        a fluid coupler that is releasably coupleable with the fluid cartridge to establish fluid flow between the fluid cartridge and the receiving device, the fluid coupler defining an opening configured to receive an insert valve of the fluid cartridge, the fluid coupler including a latch mechanism having a latch plate that is movable between: (i) a closed position in which the latch plate covers part of the opening so the latch plate engages with the insert valve of a coupled fluid cartridge and thereby locks the coupled fluid cartridge in the fluid coupler and prevents the coupled fluid cartridge from being removed from the fluid coupler and (ii) an open position in which the latch mechanism is moved away from the opening so the latch plate does not engage with the insert valve of a coupled fluid cartridge and so that the coupled fluid cartridge can be uncoupled from the fluid coupler;
        a motorized latch assembly for automatically actuating the latch mechanism to the open position in which the coupled fluid cartridge can be uncoupled from the fluid coupler; and
    a control device programmed to communicate with the receiving device and the fluid cartridge magazine assembly, wherein the control device is programmed to control, using the motorized latch assembly, a state of the latch mechanism between the open position and the closed position.

2. The system of claim 1, wherein the control device comprises a writeable memory, the memory being programmed to store one or more instructions for execution by the control device.

3. The system of claim 1, wherein the control device communicates with the receiving device through a wired connection.

4. The system of claim 3, wherein the receiving device further comprises a control unit to control the fluid cartridge.

5. The system of claim 4, wherein the control unit is configured to communicate with the fluid cartridge to determine a content of the fluid cartridge.

6. The system of claim 1, wherein the control unit is configured to communicate with the motorized latch assembly through a hub.

7. The system of claim 1, further comprising a separate device programmed to communicate with the control device using a wireless interface.

8. The system of claim 7, wherein the separate device is a smartphone, wherein the smartphone executes an application to communicate with the control device.

9. The system of claim 1, wherein the motorized latch assembly comprises:
    an electric motor;
    an eccentric cam attached via gears to a shaft of the electric motor, the eccentric cam being rotated when the shaft of the electric motor rotates; and
    the latch plate positioned to be pressed upon by the eccentric cam;
    wherein, when the eccentric cam is rotated so that the electric cam presses upon the latch plate, the latch plate moves a sufficient distance to put the latch mechanism in the open position to permit the fluid cartridge to be physically disconnected from the fluid coupler.

10. The system of claim 1, wherein the fluid cartridge includes an identifier for the fluid cartridge.

11. The system of claim 10, wherein the identifier is a radio frequency identification (RFID) tag.

12. The system of claim 10, wherein the receiving device includes one or more components to read the identifier from the fluid cartridge.

13. The system of claim 1, wherein the receiving device is a printer and the fluid cartridge contains toner or ink.

14. The system of claim 1, wherein the fluid cartridge magazine assembly is configured to releasably receive two or more fluid cartridges.

15. The system of claim 1, wherein the fluid cartridge is releasably coupleable with the fluid coupler while the latch mechanism is in the closed position.

16. The system of claim 1, wherein the latch mechanism includes a spring that acts on the latch plate to bias the latch plate to the closed position.

* * * * *